US009861735B2

(12) United States Patent
Falkenhagen et al.

(10) Patent No.: US 9,861,735 B2
(45) Date of Patent: Jan. 9, 2018

(54) EXTRACORPOREAL PERFUSION APPARATUS

(71) Applicant: Fresenius Medical Care Deutschland GmbH, Bad Homburg (DE)

(72) Inventors: Dieter Falkenhagen, Krems (AT); Jens Hartmann, Furth (AT); Stephan Harm, Furth (AT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 274 days.

(21) Appl. No.: 14/411,665

(22) PCT Filed: Jun. 27, 2013

(86) PCT No.: PCT/EP2013/063498
§ 371 (c)(1),
(2) Date: Dec. 29, 2014

(87) PCT Pub. No.: WO2014/001445
PCT Pub. Date: Jan. 3, 2014

(65) Prior Publication Data
US 2015/0157779 A1 Jun. 11, 2015
US 2015/0328387 A2 Nov. 19, 2015

(30) Foreign Application Priority Data

Jun. 28, 2012 (EP) .................................... 12174028
Feb. 28, 2013 (EP) .................................... 13157246

(51) Int. Cl.
*A61M 1/34* (2006.01)
*A61M 1/36* (2006.01)
(Continued)

(52) U.S. Cl.
CPC ......... *A61M 1/3472* (2013.01); *A61K 31/745* (2013.01); *A61K 38/12* (2013.01);
(Continued)

(58) Field of Classification Search
CPC ... A61K 31/745; A61K 38/12; A61M 1/3472; A61M 1/3486; A61M 1/3679;
(Continued)

(56) References Cited

U.S. PATENT DOCUMENTS 4,382,124 A   5/1983   Meitzner et al.
5,510,242 A   4/1996   Blais et al.
(Continued)

FOREIGN PATENT DOCUMENTS

CN   1190902 C     2/2005
CN   102361689 A   2/2012
(Continued)

OTHER PUBLICATIONS

International Preliminary Report on Patentability for International Application No. PCT/EP2013/063498, Report issued Dec. 31, 2014, dated Jan. 8, 2015, 11 Pgs.
(Continued)

*Primary Examiner* — John Kim
(74) *Attorney, Agent, or Firm* — KPPB LLP

(57) ABSTRACT

Embodiments of the invention relate to an extracorporeal perfusion apparatus comprising an extracorporeal blood circuit for conveying blood, a filtrate circuit for conveying blood plasma, and a controller, wherein the filtrate circuit is connected to the extracorporeal blood circuit by means of a filter, wherein the filter has a sieving coefficient of 5% for substances having a molar mass of 340,000 g/mol (relative molecular mass of 340 kDa), and wherein a depletion agent comprising a first carrier having a neutral, hydrophobic surface is arranged in the filtrate circuit, wherein the perfusion apparatus comprises a dispensing means for feeding an endotoxin-binding lipopeptide into the extracorporeal blood circuit, wherein the endotoxin-binding lipopeptide is selected from the group consisting of polymyxins, poly-
(Continued)

myxin derivatives, prodrugs thereof, and a combination thereof.

20 Claims, 18 Drawing Sheets

(51) Int. Cl.
| | |
|---|---|
| B01J 20/28 | (2006.01) |
| B01J 20/32 | (2006.01) |
| B01J 20/26 | (2006.01) |
| A61K 38/12 | (2006.01) |
| A61K 31/745 | (2006.01) |

(52) U.S. Cl.
CPC ........ *A61M 1/3486* (2014.02); *A61M 1/3679* (2013.01); *B01J 20/261* (2013.01); *B01J 20/264* (2013.01); *B01J 20/28004* (2013.01); *B01J 20/28016* (2013.01); *B01J 20/28019* (2013.01); *B01J 20/28061* (2013.01); *B01J 20/28064* (2013.01); *B01J 20/28066* (2013.01); *B01J 20/28083* (2013.01); *B01J 20/28085* (2013.01); *B01J 20/321* (2013.01); *B01J 20/3214* (2013.01); *B01J 20/3246* (2013.01); *B01J 20/3274* (2013.01); *A61M 2202/049* (2013.01); *A61M 2202/0413* (2013.01); *A61M 2202/0456* (2013.01); *A61M 2205/3303* (2013.01); *A61M 2205/75* (2013.01)

(58) Field of Classification Search
CPC .. A61M 2202/0413; A61M 2202/0456; A61M 2202/049; A61M 2205/3303; A61M 2205/75; B01J 20/261; B01J 20/264; B01J 20/28004; B01J 20/28016; B01J 20/28019; B01J 20/28061; B01J 20/28064; B01J 20/28066; B01J 20/28083; B01J 20/28085; B01J 20/321; B01J 20/3214; B01J 20/3246; B01J 20/3274

See application file for complete search history.

(56) References Cited

U.S. PATENT DOCUMENTS

| | | | |
|---|---|---|---|
| 5,855,782 A | | 1/1999 | Falkenhagen et al. |
| 2011/0070424 A1 | | 3/2011 | Young et al. |
| 2012/0152847 A1* | | 6/2012 | Falkenhagen .......... B01D 15/00 210/691 |

FOREIGN PATENT DOCUMENTS

| | | |
|---|---|---|
| DE | 19515554 A1 | 10/1996 |
| DE | 19913707 A1 | 10/2000 |
| DE | 102004029573 A1 | 12/2005 |
| DE | 102005046258 A1 | 3/2007 |
| EP | 110409 A2 | 6/1984 |
| EP | 129786 A2 | 1/1985 |
| EP | 168801 B1 | 11/1992 |
| EP | 776223 B1 | 6/1999 |
| EP | 787500 B1 | 12/1999 |
| EP | 958839 B1 | 12/2004 |
| EP | 1944046 B1 | 8/2010 |
| JP | 01-014788 A | 3/1989 |
| JP | 01-20903 B2 | 4/1989 |
| JP | 04-022589 B2 | 4/1992 |
| JP | 10-290833 A | 11/1998 |
| JP | 3353467 B2 | 9/2002 |
| JP | 2006508703 A | 3/2006 |
| JP | 2006320729 A | 11/2006 |
| JP | 2007089788 A | 4/2007 |
| JP | 2012515577 A | 7/2012 |
| JP | 2013523772 A | 6/2013 |
| WO | 03090924 A1 | 11/2003 |
| WO | 2005082504 A2 | 9/2005 |
| WO | 2007142611 A1 | 12/2007 |
| WO | 2010083545 A2 | 7/2010 |
| WO | 2011123767 A1 | 10/2011 |
| WO | 2011133287 A1 | 10/2011 |
| WO | 2011160149 A1 | 12/2011 |
| WO | 2014001445 A1 | 1/2014 |

OTHER PUBLICATIONS

International Search Report and Written Opinion for International Application No. PCT/EP2013/063498, Search completed Jul. 30, 2013, dated Aug. 6, 2013, 12 Pgs.
European Search Report for Application No. EP 12174028, Search Completed Nov. 14, 2012, 13 Pgs.
European Search Report for Application No. EP 13157246, Search Completed Apr. 11, 2013, 8 Pgs.
Anonymous, "Rohm and Haas AMBERCHROM CG161 Product Data Sheet", Feb. 1, 2005, XP055844261, Retrieved from URL:http://www.rohmhaas.comjionexchange/pharmaceuticals/Bioprocessingdocjus english/CG161.pdf on Nov. 14, 2012, 4 Pgs.
Falkenhagen, Dieter et al., "Fluidized Bed Adsorbent Systems for Extracorporeal Liver Support", Therapeutic Apheresis and Dialysis, Bd. 10, Nr. 2, XP055044253, ISSN: 1744-9979, DOI: 10.1111/j.1744-9987.2006.00357.x, Apr. 28, 2006, pp. 154-159.
Vincenzo, Cantaluppi et al., "Protective effect of resin adsorption on septic plasma-induced tubular injury", Critical Care. Biomed Central Ltd. London. GB. Bd. Nr., XP021070812, Jan. 11, 2010, 14 Pgs.
Weber, Viktoria et al., "Neutral Styrene Divinylbenzene Copolymers for Adsorption of Toxins in Liver Failure", Biomacromolecules 2008, Bd. 9, Nr 4, XP055043956, ISSN: 1525-7797, Mar. 18, 2008, pp. 1322-1328.
Cantaluppi, Vincenzo et al., Protective effect of resin adsorption on septic plasma-induced tubular injury, Critical Care, UK, Biomed Central Ltd., Jan. 11, 2010, Bd.14, No. 1, R4.
Falkenhagen, Dieter et al., Fluidized Bed Adsorbent Systems for Extracorporeal Liver Support, Therapeutic Apheresis and Dialysis, International Society for Apheresis, Apr. 1, 2006, Bd.10, No. 2, 1, 154-159.
Weber, Viktoria et al., Neutral Styrene Divinylbenzene Copolymers for Adsorption of Toxins in Liver Failure, Biomacromolecules, USA, American Chemical Society, Mar. 18, 2008, Bd.9, No. 4, 18, 1322-1328.
Blais et al., "Use of polymyxin-coated polyester cloth in the enzyme immunoassay of Salmonella lipopolysaccharide antigens", International Journal of Food Microbiology, Elsevier Science Publishers, Amsterdam, NL, vol. 11, No. 3-4, Dec. 1, 1990 pp. 195-204.
Cruz et al., "Effectiveness of polymyxin B-immobilized fiber col. in sepsis: a systematic review", Critical Care vol. 11, No. 3, Apr. 20, 2007.
Falagas et al., Feb. 13, 2006, Critical Care 10:R27.
Falkenhagen et al., "Fractionated plasma separation and adsorption system: a novel system for blood purification to remove albumin bound substances", Artif Organs, Jan. 1999, vol. 23, No. 1, pp. 81-6.
Garidel et al., Anti-Infective Agents in Medicinal Chemistry, Sep. 5, 2009, vol. 8, pp. 367-385.
Jiang et al., "A synthetic peptide derived from bactericidal/permeability-increasing protein neutralizes endotoxin in vitro and in vivo", International Immunopharmacology, Feb. 4, 2004, vol. 4, pp. 527-537.
Tetta et al., Nephrol Dial Transplant, 1998, vol. 13, pp. 1458-1464.
Velkov, Tony et al., Journal of Medicinal Chemistry, Mar. 11, 2010, vol. 53, No. 5, pp. 1898-1916.

* cited by examiner

EXTRACORPOREAL PERFUSION APPARATUS

FIELD OF THE INVENTION

The invention generally relates to an extracorporeal perfusion apparatus comprising an extracorporeal blood circuit for conveying blood, a filtrate circuit for conveying blood plasma, and a controller, wherein the filtrate circuit is connected to the extracorporeal blood circuit by means of a filter, wherein the filter has a sieving coefficient of 5% for substances having a molar mass of 340 000 g/mol (relative molecular mass of 340 kDa), and wherein a depletion agent comprising a first carrier having a neutral, hydrophobic surface is arranged in the filtrate circuit.

BACKGROUND OF THE INVENTION

Sepsis and associated complications contribute to a not inconsiderable extent to morbidity and mortality in humans. In most cases, sepsis can be attributed to an infection with gram-negative bacteria when high endotoxin concentrations reach the body and have a systemic effect.

Endotoxins are lipopolysaccharides (LPSs) in the cell wall of gram-negative bacteria and are released by cell lysis and cell division. In fact, lipopolysaccharides are the most common lipid component of the outer cell membrane of gram-negative bacteria. Endotoxins are pyrogenic substances, and the individual affected responds with a strong inflammatory reaction and fever when endotoxins enter the body, for example during the course of microbial poisoning, and, as key mediators, cause an uncontrolled activation of the mononuclear phagocyte system. An accumulation of endotoxins in the blood circuit as a result of endotoxemia leads to an uncontrolled activation of the immune cells and to an imbalance of the coagulation system. This can lead to sepsis, which is characterised inter alia by high fever, low blood pressure and, in severe cases, by multi-organ failure. Sepsis is a condition to be taken very seriously; the lethality of individuals with severe sepsis or septic shock is approximately 30-60% depending on the degree of severity of the condition. Endotoxemia as a result of an infection with gram-negative bacteria is one of the most common causes for the occurrence of a systemic inflammatory response ("systemic inflammatory response syndrome", SIRS), sepsis, severe sepsis or septic shock and the resultant serious complications. Patients with jeopardised immune defence, such as liver patients or chemotherapy patients, are susceptible to bacterial infections and thus display symptoms of endotoxin poisoning. Endotoxemia may also occur in the case of acute liver failure or acute decompensation with chronic liver failure, thus resulting in the development of states that are very similar (from a biochemical viewpoint) to sepsis. By way of example, acute decompensation may occur in patients with chronic liver failure. In this state, the endotoxins originating from the normal intestinal flora pass the intestinal barrier and stimulate the release of inflammation mediators in the body and therefore cause a sepsis-like state.

Furthermore, septic states can also be triggered by gram-positive bacteria, viruses and fungi.

As mentioned, it is generally known that an uncontrolled activation of the immune cells and an imbalance of the coagulation system may occur in the case of sepsis and other serious conditions. The uncontrolled activation of the mononuclear phagocyte system stimulates an excessive release of inflammation mediators, in particular of cytokines (also referred to as cytokine storm or hypercytokinemia). Cytokines are key mediators in the case of sepsis and septic shock. Tumour necrosis factor (TNF-α, often also referred to merely as TNF) and interleukin-1β (IL-1β) can be cited as the most important pro-inflammatory examples. Further important pro-inflammatory cytokines include IL-6 and IL-8. The initially released cytokine TNF-α triggers a biological signal amplification via a mediator cascade, thus resulting in physiological changes, including severe disruptions to the biological balance and subsequently to circulatory collapse and multi-organ failure. The clinical picture of sepsis correlates with high blood concentrations of the key mediator TNF-α, but also of other cytokines, such as IL1-β, IL-6 and IL-8 in the case of the pro-inflammatory phase or IL-10 or IL-13 with the occurrence of an anti-inflammatory phase, in which the pro-inflammatory mediators inclusive of cytokines have very low concentrations. Furthermore, other serious conditions, such as chronic inflammatory intestinal diseases, psoriasis and rheumatoid arthritis are also associated with excessive TNF-α release.

Besides the intensive medical treatment applied as standard, antibiotics or corticosteroids, immunoglobulins and also circulation-assisting drugs in particular are used for the treatment of sepsis.

A disadvantage of antibiotic therapy is the increasing spread of antibiotic-resistant bacteria. Furthermore, endotoxins are increasingly released by the antibiotic and the accompanying destruction of the bacteria cells, which in turn leads to an increased distribution of inflammation mediators. In addition, an administration of antibiotics is often associated with side effects, such as changes to the intestinal flora or allergic reactions. The attempt to use antibiotics against the key factor TNF-alpha failed, since with this method the reduction of the TNF concentration to zero or very low values appeared to trigger an anergic situation, which was accompanied by a higher mortality compared with the control group. The therapeutic use of specific antibodies against LPS and TNF-α is technically very complex and is therefore associated with high costs.

By means of extracorporeal blood or plasma purification systems (therapeutic apheresis method), it is therefore attempted, as will be described in greater detail hereinafter, to remove the aforementioned cytokines, in particular the factor TNF-α, in such a way as to normalise the concentrations of these cytokines so as to thus avoid the anergic (anti-inflammatory) phase. Endotoxins can be eliminated by means of what are known as LPS-adsorbers (for example the adsorber Toraymyxin®) so as to thus avoid a release of the pro-inflammatory cytokines, which naturally also reduces the anti-inflammatory response.

Apheresis methods are methods carried out extracorporeally, in which pathophysiologically relevant blood and plasma components, for example biomolecules such as (glycol) proteins, peptides, lipids, lipoproteins and lipopolysaccharides, but also blood cells and blood plasma, are removed. Apheresis methods can be used on the one hand for diagnostic and therapeutic purposes, but on the other hand also constitute a very effective possibility for obtaining certain blood components from healthy individuals in sufficient quantity and with sufficiently high purity. Great importance is attributed to therapeutic apheresis, since, with certain indications, this is often a very effective alternative, at the same time having few side effects, compared to treatment with drugs. In the case of plasma apheresis methods, the plasma can thus either be completely separated or replaced by a substitute solution, or only certain components, such as cytokines LDL, endotoxins or immunoglobulins, are removed therefrom by means of an adsorber, and the plasma is then returned again to the donor/patient. Compared with the aforementioned treatment strategies using drugs, therapeutic apheresis methods also have the advantage that the treatment is stopped at any time with immediate effect by switching off the apheresis apparatus.

Apheresis methods and adsorber materials for eliminating toxic and/or harmful blood components are well known in the prior art. Adsorber materials which specifically adsorb cytokines, in particular TNF-α, and/or endotoxins (LPSs), and remove these from bodily fluids such as blood or plasma are also known.

Document US 2001/0070424 A1 discloses an adsorber material based on a porous polymer, which has at least one transport pore with a diameter from 25 to 200 nm and also effective pores with a diameter from 10 to 25 nm. Inter alia, the polymer may also be a non-ionic resin (neutral resin). The adsorber is used to remove protein molecules, in particular cytokines and β2 microglobulin.

Document WO 2011/123767 A1 discloses a method for treating inflammation, wherein a therapeutically effective dose of porous adsorber particles for adsorbing inflammation mediators is administered to a patient, wherein the total pore volume with a pore size from 5 to 300 nm is greater than 0.5 cc/g to 3.0 cc/g.

In WO 2003/090924 a porous separation matrix for separating blood components is described in conjunction with inflammation processes. The separation matrix has a pore size from 5 μm to 500 μm and also at least one functional group arranged on the matrix.

DE 19515554 A1 discloses methods and apparatuses for simultaneous extracorporeal elimination of TNF-α and lipopolysaccharides from whole blood and/or blood plasma. Here, the blood or blood plasma is guided in an extracorporeal perfusion system via a porous cation exchanger material and an anion exchanger material. The porous carrier materials described therein have a mean pore diameter of <30 nm and/or a molecular exclusion size for globular proteins of <$10^6$ Dalton and in particular <$2 \times 10^4$ Dalton.

Neutral resins for removing toxic components, including cytokines, from a bodily fluid are also disclosed in WO 2005/082504 A2. WO 2005/082504 A2 describes a detoxification apparatus, which comprises activated carbon and at least one non-ionic resin having a mean pore size of 30 nm and a mean particle diameter of 35-120 μm (Amberchrom CG300C) or having a means pore size of 45 nm and mean particle diameter of 560 μm (resin based on aliphatic esters-Amberlite XAD-7HP).

EP 0787500 B1 and EP 0958839 B1 disclose a hydrophobic carrier material having a pore size from 10 to 30 nm and particle sizes from 20 to 350 μm, preferably 10 to 100 μm or 250 to 350 μm, for removing toxic components, in particular cytokines, from a bodily fluid.

EP 1 944 046 B1 discloses a carrier material based on a polystyrene-divinylbenzene copolymer having a pore size of 30 nm and a particle size from 75 to 120 μm.

Tetta et al. (Tetta et al. 1998. Nephrol Dial Transplant 13:1458-1464) describe an adsorber of the Amberchrom CG 300md type having a pore size of 30 nm for removing cytokines from a bodily fluid.

The publication by Cantaluppi et al. (Cantaluppi et al. 2010. Critical Care 14:R4) describes an adsorber of the Amberchrom CG161m type for cytokine adsorption.

It has also been found that anion exchanger resins (for example DEAE or PEI groups bound to cellulose) are very well suited for endotoxin binding. However, the undesirable binding of key factors of the intracorporeal coagulation system, such as protein C and protein S, and the associated coagulation problems are disadvantageous. These coagulation problems can be avoided by the use of a specific adsorber which comprises immobilised antibodies against endotoxins. However, this possibility can only be applied to a limited extent for economical reasons.

In DE 199 13 707 A1, an immune adsorber for use in sepsis therapy for plasmapheresis is described, consisting of a carrier material formed from organic or synthetic polymers and polyclonal or monoclonal antibodies bonded thereto and directed against complement factors, lipopolysaccharides and also against further sepsis mediators, such as TNF-α and interleukins.

DE 10 2004 029 573 A1 discloses an apheresis material or adsorbent and also a method for removing, depleting or inactivating the cytokine MIF (macrophage migration inhibitory factor) from blood, blood plasma or other bodily fluids. The adsorbent comprises a fixed carrier material on the surface of which MIF-binding molecules or functional groups are immobilised.

DE 10 2005 046 258 A1 discloses an immune adsorber for treating insulin resistance and/or the metabolic syndrome, wherein the immune adsorber comprises carrier materials with bonded ligands which are specific for IL-6, IL-4 and C5a.

A therapy form already used for a long time in clinical application is constituted by the parenteral administration of polymyxins. Polymyxins are antibiotic substances which originate initially from the bacteria *Bacillus polymyxa* and which have already been used for decades in humans and animals in order to treat infections with gram-negative bacteria. Polymyxins interfere with the cell wall structure by increasing the permeability of the cell membrane, thus resulting in cell lysis. Polymyxins bind not only phospholipids, but also endotoxins (LPS) so as to form a polymyxin-endotoxin (LPS) complex with high affinity. The anti-bacterial mechanism of polymyxins is described in detail for example in a publication by Tony Velkov et al. (Tony Velkov et al. 2010. Journal of Medicinal Chemistry: 53(5):1898-1916).

Due to the neurotoxic and nephrotoxic effect of polymyxins, only polymyxin B and polymyxin E (Colistin) have gained a certain therapeutic importance as antibiotic. Until now, these two polymyxins were the only therapeutically admissible representatives of their substance class. Polymyxin B and Colistin are authorised in the USA by the FDA for parenteral infusion. Polymyxin B and Colistin have been used for decades for oral or topical therapy forms. However, for parenteral systemic treatment of conditions and states caused by an infection with gram-negative bacteria, they are only used as antibiotic in a therapeutic context as a last resort due to their neurotoxic and nephrotoxic side effects. Colistin appears to be less nephrotoxic than polymyxin B, however this is offset at least in part by the necessary higher dosing, and therefore nephrotoxic reactions are to be expected to approximately the same extent in everyday clinical practice. However, there is not currently sufficient data available regarding the nephrotoxicity of the two antibiotics. Infectologists from New York (USA) describe kidney failure in 14% of 60 patients treated with polymyxin B. Doctors in Greece describe significant nephrotoxicity in the majority of patients in which renal insufficiency was already present at the start of therapy. By contrast, in patients with normal kidney function, no significant changes were established. A detailed overview concerning the toxicity of polymyxins can be found in a publication by Falagas and Kasiakou (Falagas and Kasiakou. 2006. Critical Care 10:R27). The dosing of polymyxins consequently plays a central role in the avoidance or minimisation of toxic side effects, in particular nephrotoxic side effects.

Due to the occurrence, observed frequently in recent years, of severe progressions of disease caused by infections with multi-resistant pathogenic strains, for example in the case of acute infections with strains of the bacterium *Pseudomonas aeruginosa*, polymyxins are increasingly being administered parenterally as antibiotic by necessity, in spite of their toxicity. A source of supply for polymyxin B in the form of the sulphate salt of polymyxin B1 and B2 for parenteral administration is currently offered by Bedford Laboratories ("Polymyxin B for Injection 500 000 Units", manufacturer: Bedford Laboratories). In accordance with manufacturer information, the parenteral administration is carried out intravenously, intramuscularly or, in the case of meningitis, intrathecally, wherein the specified maximum daily dose is generally 2.5 mg/kg body weight per day, divided between two to three infusions. The serum concentration of polymyxin following administration typically lies in a range from 1 to 6 µg/ml. in severe cases this may also be higher in a range from 6 to 50 µg/ml. Colistin is administered predominantly in the form of Colistin methanesulfonate, wherein the serum concentration lies in a range from approximately 1 to 3 µg/ml. Colistin (polymyxin E) is used in a manner similar to polymyxin B, usually in higher dosage.

A resistance to polymyxin B is rather unusual, but may develop if the antibiotic does not reach the cytoplasma membrane due to changes in the outer membrane. Polymyxins are effective against many gram-negative pathogens, such as *E. coli, Enterobacter. Klebsiella* spp. and also against *P. aeruginosa. Proteus* types and *S. marcescens*, which are normally resistant; the sensitivity of *B. fragilis* is variable. The minimum inhibitory concentrations for *E. coli* lie in the range from 0.04-3.7 mg/l and for *P. aeruginosa* between 1.2 and 33.3 mg/l (Garidel and Brandenburg. 2009. Anti-Infective Agents in Medicinal Chemistry, 8:367-385).

Since the dosages for polymyxin B and Colistin used previously in clinical application in the case of parental administration induce nephrotoxic and neurotoxic side effects, new treatment strategies and therapy approaches have been developed in the past in conjunction with the application of endotoxin-binding lipopeptides such as polymyxin.

The extracorporeal blood and/or blood plasma purification methods, already mentioned previously, with use of suitable adsorber materials have become established as frequently applied alternatives to the administration of polymyxins in the form of a drug.

Known adsorber materials comprise porous or fibre-like carrier materials, on the surfaces of which polymyxin B is immobilised. Known neurotoxic and nephrotoxic side effects have been reported previously in conjunction with adsorber materials of this type, which are used to a large extent in the treatment of septic states.

In EP 0110 409 A, polymyxin B-immobilised carriers formed from porous glass (FPG 2000) and also polymyxin B-immobilised polysaccharide carriers based on cellulose (Cellulofine A-3) are disclosed. Microparticles formed from cellulose or derivatised cellulose, to which polymyxin B is covalently bonded, are also known (Weber V., Loth F., Linsberger I., Falkenhagen D.: Int. J. Artif. Organs 25(7), 679). EP 0 129 786 A2 describes an endotoxin detoxification material with a fibre-like carrier, on which polymyxin is covalently immobilised. The fibre-like carrier is equipped with functional groups in order to bind polymyxin covalently to the surface of the carrier. Disadvantages of the specified endotoxin adsorbers include the low endotoxin binding capacity and speed. The efficacy and quality of the treatment in relation to fibre-like carriers with covalently bonded polymyxin B have been described as sub-optimal (Cruz D N et al. 2007. Effectiveness of polymyxin B-immobilized fiber column in sepsis: a systematic review. Crit. Care 11(3):137).

WO 2010/083545 and WO 2011/160149 describe adsorber materials with which polymyxin is immobilised on hydrophobic carrier surfaces via non-covalent interactions (adsorption). WO 2007/142611 A1 and U.S. Pat. No. 5,510,242 describe hydrophobic carrier surfaces with adsorptively bonded polymyxins. The use of polymyxin-coated polyester fabrics for binding LPS antigens of *Salmonella typhimurium* was described by Blais and Yamazaki (Blais and Yamazaki. 1990. Use of polymyxin-coated polyester cloth in the enzyme immunoassay of Salnmonella lipopolysaccharide antigens. International journal of Food Microbiology 11:195-204).

WO 2011/133287 A1 discloses a blood filtration apparatus, which comprises a microfluidic separation apparatus and with which undesirable substances such as toxins, drugs, pathogens and the like, can be removed from the blood. The apparatus may comprise sensors which monitor the blood in terms of the presence or concentration of the undesirable substances. The monitoring may also include the infusion of therapeutic active ingredients, such as an antibiotic, into the blood of the patient.

An extracorporeal perfusion apparatus of the type mentioned in the introduction has been described for example by Falkenhagen et al. (Falkenhagen et al. 2006. Fluidized Bed Adsorbent System for Extracorporeal Liver Support. Therapeutic Apheresis and Dialysis 10(2):154-159). The filter described therein is obtainable under the trade name "Albuflow®" (Fresenius Medical Care, Germany).

Although the lethality of patients suffering from endotoxemia-induced conditions, in particular sepsis, could be reduced by the clinical application of the above-mentioned polymyxin-based adsorber materials, the lethality of patients with severe sepsis and septic shock is still very high in spite of maximum therapy. For this reason and also due to the ever-increasing problem of the multi-resistance of bacteria to antibiotics and the associated rising incidence of severe progressions of disease, there is also a high demand for improved therapy forms and more efficient extracorporeal perfusion apparatuses, which additionally are quite safe in clinical application.

SUMMARY OF THE INVENTION

The object of many embodiments of the invention is therefore to provide an extracorporeal perfusion apparatus of the type mentioned in the introduction, with which an improved treatment of sepsis and sepsis-like states is possible.

The object is achieved by an extracorporeal perfusion apparatus of the type mentioned in the introduction, which is characterised in accordance with many embodiments of the invention in that the perfusion apparatus comprises a dispensing means for feeding an endotoxin-binding lipopeptide into the extracorporeal blood circuit, wherein the endotoxin-binding lipopeptide is selected from the group consisting of polymyxins, polymyxin derivatives, prodrugs thereof and a combination thereof.

Thanks to numerous embodiments of the invention, an improved treatment of sepsis and sepsis-like states compared to the previously known therapy approaches is possible.

A first major advantage of the perfusion apparatus according to many embodiments of the invention lies in the fact that the filter not only constitutes a barrier for endotoxins and other high-molecular plasma components, but also for the formed endotoxin-lipopeptide complexes, such that endotoxin-lipopeptide complexes present in the blood of the patient, which circulate in the extracorporeal blood circuit prior to being broken down in the liver, cannot enter the filtrate circuit and cannot reach the carrier. Contact with the carrier, due to competitive interaction processes between complex and first carrier surface, would lead to a dissolution of the endotoxin-lipopeptide complex, whereby this may worsen the state of a patient with sepsis. The renewed supply of endotoxins caused by the dissociation of the lipopeptide-endotoxin complexes causes a renewed intensification of the activation process of the complement or coagulation system and also cellular systems (monocytes) caused by endotoxins, these activation processes being associated with corresponding clinical consequences such as the initiation or intensification of multi-organ failure or the initiation of the anergic stage of sepsis, that is to say the stage in which the immune system is weakened. The consequence of this means that the release of endotoxins should be prevented in any case.

Thanks to a number of embodiments of the invention, endotoxin-binding lipopeptides can be fed to the blood by means of the dispensing means, and endotoxins can be eliminated by complex formation, and at the same time undesirable blood components, in particular cytokines, can be depleted by the depletion agent, whereby maximum therapy without additional safety risk for the patient is possible.

A further key advantage of the perfusion apparatus according to many embodiments of the invention also lies in the fact that undesirable blood components, in particular cytokines, can be removed from the blood plasma by adsorption at the surface of the first carrier due to the depletion agent arranged in the filtrate circuit. The inventors have surprisingly found that the adsorption efficiency for cytokines, first and foremost TNF-α, with use of the filter used in accordance with numerous embodiments of the invention is significantly better compared with a plasma filter that retains only cellular blood components, although fewer cytokines from the extracorporeal blood circuit pass through the filter into the fractionated plasma conveyed in the filtrate circuit. The filter used in accordance with many embodiments of the invention practically completely prevents the permeation of proteins or lipoproteins and glycoproteins having a relative molar mass above 300,000. It has been found that this advantage guarantees a much better reproducibility of the cytokine elimination compared with the use of a plasma filter that retains only cellular components.

The filter used in accordance with a number of embodiments of the invention allows fractionated blood plasma to pass through, such that high-molecular blood components, endotoxins and also endotoxin-lipopeptide complexes are retained, whereas smaller blood components can pass through the filter membrane. A suitable filter is obtainable under the trade name "Albuflow®" (manufacturer: Fresenius Medical Care; material: polysulfone hollow fibres; sieving coefficient for albumin of ≥0.6 and for fibrinogen ≤0.1).

The term "blood plasma" used herein, in so far as this is conveyed in the filtrate circuit of the apparatus according to many embodiments of the invention, therefore relates to fractionated blood plasma.

The expression "carrier having a neutral, hydrophobic surface" within the scope of this disclosure relates to a water-insoluble solid, which has a neutral and hydrophobic surface. The term "neutral" is to be understood non-ionically. The carrier can be in fibre or particle form. The carrier may also be porous and may have outer and inner surfaces. The outer and inner surfaces are neutral and hydrophobic. The term "inner surface" of the carrier denotes the totality of the surfaces of the pores. The term "outer surface" by contrast relates to the totality of the surfaces of the carrier that are directly accessible from outside.

The terms "polymyxin" and "polymyxins" as used herein relate to known, naturally occurring chemical compounds which originate initially from the bacterium *Bacillus polymyxa* (polymyxin B) and also *Bacillus colistinus* (polymyxin E). The polymyxins can either be isolated from bacteria or can be produced synthetically. Polymyxin B originating from the bacterium is composed of 6 derivatives referred to as polymyxin B1, polymyxin B2, polymyxin B3, polymyxin B4, polymyxin B5 and polymyxin B6. By contrast, the polymyxin authorised by the FDA for parenteral infusion is composed only of polymyxin B1 to B4. As mentioned previously, only polymyxin B and Polymyxin E (Colistin) are of clinical relevance.

The term "prodrug" as used herein relates to precursor compounds of polymyxins as defined above, wherein the precursor compounds are converted in vivo into the active polymyxin. Representative examples include the prodrugs Colistin methanesulfonate and polymyxin B methanesulfonate sodium.

The term "polymyxin derivative" relates to a compound derived from polymyxin, which compound is obtainable by modification of naturally occurring polymyxins, for example by chemical modification of the Dab side chains, the cyclic peptide ring or the fatty acid chain of the polymyxin molecule structure. A detailed overview of polymyxin-based antibiotics, analogues and derivatives is described in the publication by Velkov et al. (Velkov et al. 2010. Journal of Medicinal Chemistry, 53(5):1898-1916). The suitability of a polymyxin derivative for use in many embodiments of the present invention can be tested by a person skilled in the art on the basis of simple routine tests.

The term "endotoxemia" is used herein for all disease patterns in which clinically relevant quantities of endotoxins are found in the blood of the patient and lead subsequently to disease patterns such as sepsis and SIRS.

The term "depletion agent" relates to an agent with which undesirable components can be removed from the blood plasma conveyed in the filtrate circuit. Depletion agents that comprise a carrier having a neutral, hydrophobic surface have proven themselves in the past to be particularly favourable for the elimination of inflammation mediators such as cytokines by adsorption at the carrier surface thereof. These cytokines are advantageously potentially harmful pro-inflammatory cytokines. Representative examples for pro-inflammatory cytokines include TNF-α, IL-1β, IL-6 and IL-8, wherein TNF-α is of particular importance as an initial pro-inflammatory inflammation mediator. The depletion agent used in accordance with a number of embodiments of the invention is therefore particularly favourable for the treatment of conditions and states attributed to the toxic effects of TNF-α. By way of example, in the case of sepsis, the values for the TNF-α in the pro-inflammatory phase are at least greater than 100-200 ng/ml. The examples specified below provide proof that TNF-α, IL-10, IL-6, IL-8 and also the anti-inflammatory IL-10 are eliminated as efficiently as possible and that the apparatus according to many embodiments of the invention is extraordinarily well suited for the treatment of sepsis, septic shock and sepsis-like states.

The expression "dispensing means for feeding an endotoxin-binding lipopeptide into the extracorporeal blood circuit" relates on the one hand to dispensing means for feeding the lipopeptide directly into the extracorporeal blood circuit. On the other hand, this expression also relates to dispensing means for indirectly feeding the lipopeptide into the extracorporeal blood circuit in that the lipopeptide is dispensed into the filtrate circuit by the dispensing means and the lipopeptide then passes from there into the extracorporeal blood circuit.

Since naturally occurring polymyxins, which originate initially from the bacteria *Bacillus polymyxa* and also *Bacillus colistinus*, are among the peptide antibiotics studied to the greatest extent and have already been used for decades in the treatment of conditions and states caused by endotoxemia, it is preferable if the endotoxin-binding lipopeptide is a polymyxin. The lipopeptide is particularly preferably selected from the group consisting of the only polymyxins previously authorised for clinical use: polymyxin B and Colistin (polymyxin E) and prodrugs thereof. Representative examples include the prodrugs Colistin methanesulfonate and polymyxin B methanesulfonate sodium. However, polymyxin B and prodrugs thereof is most preferred since this has proven to be the most successful for use in the field of human medicine.

In accordance with a first advantageous embodiment, the depletion agent comprises the dispensing means for feeding the endotoxin-binding lipopeptide, wherein the surface of the first carrier of the depletion agent has an adsorptive coating formed from the endotoxin-binding lipopeptide. In this embodiment, the depletion agent thus also acts as a dispensing means for the endotoxin-binding lipopeptide, since the first carrier is coated adsorptively with the lipopeptide. The lipopeptide is released into the filtrate circuit continuously by desorption in small quantity and is fed further from there to the extracorporeal blood circuit. The lipopeptide is thus fed into the extracorporeal blood circuit by dispensing of the lipopeptide (desorption from the first carrier) into the filtrate circuit, where it then passes on into the blood circuit. In a sub-variant, the filtrate circuit can be formed as an open filtrate circuit, which leads downstream of the filter into the extracorporeal blood circuit. In another sub-variant, the filtrate circuit can be formed as a circuit that is closed in the filtrate region and that leads into the filter. It has been found in laboratory tests that the adsorptive coating of the carrier surface with the lipopeptide has no disadvantageous effects on the adsorption of the cytokines (see Example 11 below).

The term "adsorptive coating" used in this disclosure is to be understood to mean that the endotoxin-binding lipopeptides bind to the neutral, hydrophobic carrier surface via non-covalent, adsorptive processes and interactions. It is to be assumed that in particular the hydrophobic interaction plays an important role. The hydrophobic interaction is of great biochemical importance and is based on the phenomenon that hydrophobic molecules in a polar environment tend toward association. The hydrophobic interaction therefore is not a force per se, but is enforced by a polar environment. Other non-covalent interactions, including, without limitation, ionic bonds, hydrogen bridge bonds and van der Waals interactions, may also play a role in the adsorption of endotoxin-binding lipopeptides such as polymyxin. The binding of endotoxin-binding lipopeptides such as polymyxin via non-covalent interactions to hydrophobic carrier surfaces of various pore and particle sizes has already been described in WO 2010/083545, WO 2011/160149, WO 2007/142611 A1 and U.S. Pat. No. 5,510,242. The endotoxin-binding lipopeptide bound adsorptively on the carrier is selected in accordance with a number of embodiments of the invention from the group consisting of polymyxins, prodrugs thereof, and a combination thereof.

Alternatively to the first embodiment, the dispensing means for feeding the endotoxin-binding lipopeptide is arranged in the filtrate circuit downstream of the depletion agent in a second advantageous embodiment, wherein the dispensing means comprises a second carrier having a neutral, hydrophobic surface, wherein the surface of the second carrier has an adsorptive coating formed of the endotoxin-binding lipopeptide. The lipopeptide is released continuously into the filtrate circuit by desorption in small quantity and is then fed further from there to the extracorporeal blood circuit. The lipopeptide is thus fed into the extracorporeal blood circuit by dispensing of the lipopeptide (desorption from the second carrier) into the filtrate circuit, where it then passes on into the blood circuit. In a sub-variant of the second embodiment, the filtrate circuit can be formed as an open filtrate circuit, which leads downstream of the filter into the extracorporeal blood circuit. In another sub-variant of the second embodiment, the filtrate circuit can be formed as a circuit that is closed in the filtrate region and that leads into the filter. Due to the lower design/equipment outlay however, the first embodiment is preferred compared with the second embodiment.

The development of the two above-mentioned embodiments (first and second embodiment) of the perfusion apparatus according to the invention is based on the surprising fact that with carriers that have a neutral, hydrophobic surface and that have an adsorptive coating formed of polymyxin, the endotoxin elimination is not implemented, as previously assumed, by adsorption of the endotoxins at the polymyxin molecules immobilised on the carrier, but via a very small quantity of desorbed polymyxin molecules that have transferred into the blood or blood plasma. This surprising and unforeseeable finding is based on the fact that, following selective washing of a carrier coated adsorptively with polymyxin, no endotoxin adsorption could be determined by the polymyxin molecules still immobilised on the carrier surface. The inventors could therefore determine that the excellent endotoxin elimination efficiency of neutral, hydrophobic carrier polymers, on the surfaces of which polymyxin is adsorptively bonded, is to be attributed to a very small quantity of free polymyxin molecules desorbed from the carrier material and released into the bodily fluid, that is to say blood or blood plasma. The finding that the small quantities of released polymyxin, which, depending on the polymyxin quantity adsorbed at the carrier, give a polymyxin serum concentration from approximately 0.01 μg/ml to approximately 0.8 μg/ml, are already sufficient to inhibit the activity of endotoxins, wherein neurotoxic and nephrotoxic side effects are excluded, was also surprising.

Only on the basis of this surprising finding was it possible for the inventors to develop the first and second advantageous embodiments of the perfusion apparatus according to the invention. Before this, it was always assumed that the endotoxin elimination was implemented by binding of the endotoxins to the polymyxin molecules adsorbed at the carrier. In view of the fact that a filter with a sieving coefficient of 5% for substances with a molar mass of 340

000 g/mol (relative molecular mass of 340 kDa) constitutes a barrier for endotoxins (LPS) and the endotoxins therefore cannot reach an adsorber material for endotoxins arranged in the filtrate circuit, there would have been an incentive for the first time, in the knowledge of this new surprising fact, to combine with a filter of this type a carrier that has an adsorptive coating with an endotoxin-binding lipopeptide and that dispenses a predefinable quantity of lipopeptide into the blood plasma. Due to the dispensing means arranged in the filtrate circuit, a prolonged release of very small and above all uniform quantities of endotoxin-binding lipopeptides into the blood plasma conveyed in the filtrate circuit over the total treatment period, preferably from 4 to 10 hours daily over a period from 2 to 8 days, is therefore achieved by the dispensing means arranged in the filtrate circuit. From here, the lipopeptides pass into the extracorporeal blood circuit, where they form a complex with the endotoxins (LPS) located in the blood and therefore make these harmless. Thanks to the filter, these complexes as already described above can no longer pass into the filtrate circuit and be dissolved again, whereby patient safety is kept high. The endotoxin-lipopeptide complexes are then broken down predominantly in the liver of the patient.

The endotoxin-binding lipopeptide adsorbed at the surface of the first or second carrier is preferably present in a quantity which, when the lipopeptide is dispensed, gives a lipopeptide serum concentration from 0.01 µg/ml to 0.8 µg/ml as already mentioned. It has surprisingly been found that the very low desorption of the lipopeptide from the first or second carrier is sufficient to obtain lipopeptide serum concentrations from 0.01 µg/ml to 0.8 µg/ml. It has been found that at these serum concentrations the activity of endotoxins is inhibited, wherein neurotoxic and nephrotoxic effects are to be excluded. The lipopeptide serum concentration preferably lies in a range from 0.1 µg/ml to 0.6 µg/ml, preferably 0.1 µg/ml to 0.4 µg/ml, most preferably between 0.1 µg/ml to 0.25 µg/ml, since at these serum concentrations, even with severe progressions of disease such as sepsis, severe sepsis or septic shock, efficient therapy can be carried out without neurotoxic and nephrotoxic side effects.

The first or second carrier preferably has a total surface from 100 to 1500 $m^2/g$, wherein 50 to 2000 mg are bound adsorptively at the surface of the first or second carrier to endotoxin-binding lipopeptide in relation to the total carrier surface. In this way, a lipopeptide serum concentration from approximately 0.01 µg/ml to approximately 0.8 µg/ml can be obtained by desorption of the endotoxin-binding lipopeptide from the carrier surface. For a person skilled in the art, the anticipated lipopeptide serum concentration in relation to the used carrier under consideration of the average pore size and/or average particle size can be determined on the basis of simple routine tests and calculations; calculation examples are specified further below in the examples.

Alternatively to the above-mentioned embodiments, which are based on the desorption of very low quantities of the lipopeptide from a carrier surface, the dispensing means for feeding the endotoxin-binding lipopeptide comprises a dosing device in accordance with a third advantageous embodiment for feeding the endotoxin-binding lipopeptide into the extracorporeal blood circuit at a lipopeptide feed point associated with the extracorporeal blood circuit. The lipopeptide feed point is preferably arranged downstream of the filter. If a dialyser is additionally arranged in the extracorporeal blood circuit downstream of the filter, it is then favourable if the lipopeptide feed point in the extracorporeal blood circuit is arranged downstream of the dialyser. In a sub-variant of the third embodiment, the filtrate circuit can be formed as an open filtrate circuit, which leads downstream of the filter into the extra corporeal blood circuit. In another sub-variant of the third embodiment, the filtrate circuit can be formed as a circuit that is closed in the filtrate region and that leads into the filter.

In this embodiment, the lipopeptide is infused into the extracorporeal blood circuit by means of a dosing device. The lipopeptide is preferably present in the form of a preparation for parental administration, for example as an infusion solution. The preparation may optionally comprise at least one pharmaceutically acceptable carrier and/or excipient. The preparation may comprise only one type of an endotoxin-binding lipopeptide or a mixture of two or more lipopeptides, for example a mixture of polymyxin B1, B2, B3 and B4. A "pharmaceutically acceptable carrier and/or excipient" may be any substance that is known for production of parenteral administration forms such as injections, infusion solutions and the like. Formulations for infusion solutions suitable for many embodiments of the invention are specified further below in Examples 4 and 5.

The endotoxin-binding lipopeptide is preferably present in the form of a lyophilised powder for production of a sterile aqueous injection preparation or infusion preparation, wherein the powder can be dissolved for example in sterile water, 5% dextrose solution, a ringer solution or a physiological sodium chloride solution. Polymyxin B is preferably used in the form of polymyxin B sulphate. The lipopeptide is present in the preparation in dissolved form, preferably in a concentration from 0.04 mg/l to 13 mg/l, more preferably from 0.1 mg/l to 7 mg/l, most preferably from 0.5 mg/l to 4 mg/l. The dosing is preferably set such that the lipopeptide serum concentration lies in range from 0.1 µg/ml to 0.6 µg/ml, preferably 0.1 µg/ml to 0.4 µg/ml, most preferably between 0.1 µg/ml to 0.25 µg/ml, since at these serum concentrations an efficient therapy can be carried out without neurotoxic and nephrotoxic side effects, even with severe progressions of disease, such as sepsis, severe sepsis or septic shock.

The dosing device is formed, as is known per se by a person skilled in the art, by infusion units that typically comprise a container containing the infusion solution (for example infusion bag or infusion bottle), a tube system and a pump means for dosing a desired volume per unit of time.

The infusion rate is dependent on the serum half-life for the lipopeptide in the patient. By way of example, the serum half-life for polymyxin B in patients with normal kidney function is typically 13 hours, and that for Colistin is 6 to 7.4 hours in accordance with the literature. In the case of treatment by means of the perfusion apparatus, the clearance of the filter and/or the clearance of the depletion agent for the administered lipopeptide is also to be taken into consideration, as described in detail further below. Formulations for infusion solutions suitable for this purpose and also dosing instructions are specified further below in the examples.

In order to monitor the concentration of the endotoxin-binding lipopeptide and in order to be able to adjust the dosing of the infusion solution accordingly, it is advantageous if a measuring means for measuring the concentration of the endotoxin-binding lipopeptide is arranged downstream of the filter or dialyser and upstream of the lipopeptide feed point. Suitable measuring means, for example sensors, which can be used for this purpose are described in the prior art, for example by Jiang et al. (Jiang et al. 2004. A synthetic peptide derived from bactericidal/permeability-increasing protein neutralizes endotoxin in vitro and in vivo. International Immunopharmacology 4:527-537). For the measurement, a small quantity of blood is preferably conveyed from the extracorporeal blood circuit via a branch line to the measuring means/sensor and is rejected once the concentration has been determined. An insertion of the measuring means/sensor directly into the extracorporeal blood circuit is indeed possible in principle, but is less preferable, since in this case high demands are placed on the state of the measuring means/sensor in terms of sterility and biocompatibility. For these reasons, the variant with the branch line to the measuring means/sensor is to be preferred.

The perfusion apparatus may also be assigned a control circuit controlled by means of the controller, wherein, by actuating the infusion pump, the infused quantity of the lipopeptide is controlled with respect to a predefinable target value or target value range depending the lipopeptide current value (lipopeptide serum concentration) measured by the measuring means. The target value or target value range of the lipopeptide serum concentration typically lies in a range of 0.01-0.8 µg/ml.

With the third embodiment it is also advantageous if the controller of the perfusion apparatus is designed, when dosing the lipopeptide into the blood conveyed in the extracorporeal blood circuit, to take into consideration the lipopeptide clearance of the body, the lipopeptide clearance of the depletion agent and/or the lipopeptide clearance of the dialyser. By way of example, it is known that carriers formed of a polystyrene divinylbenzene copolymer, besides pathophysiologically relevant components such as cytokines, also adsorb lipopeptides such as polymyxins, such that the consideration of the lipopeptide clearance of the first carrier (that is to say carrier of the depletion agent) is advantageous for the dosing of the infused lipopeptide.

Alternatively to the above-mentioned embodiments, the dispensing means for feeding the endotoxin-binding lipopeptide comprises, in a fourth embodiment, a dialyser, which is arranged in the extracorporeal blood circuit downstream of the filter and which is designed to feed the endotoxin-binding lipopeptide to the extracorporeal blood circuit by means of a dialysis fluid conveyed through the dialyser. In a sub-variant, the filtrate circuit can be formed as an open filtrate circuit, which leads downstream of the filter into the extracorporeal blood circuit. In another sub-variant, the filtrate circuit can be formed as a circuit that is closed in the filtrate region and that leads into the filter. The used dialysers are preferably hydrophilic polysulfone membranes with a surface of 1.4-2.0 m$^2$, which have been produced by blending with PVP (polyvinylpyrrolidone). By way of example, these membranes are used in filters provided by the company Fresenius Medical Care, inter alia in the models AF 1000 and FX60. These dialysis filters have a sieving coefficient for albumin below 0.1%. The use of what is known as a high cut-off filter, which is also based on the use of hydrophilic polysulfone membranes having a sieving coefficient of approximately 4% for albumin, is also conceivable. Under dialysis conditions, that is to say a diffusion-controlled elimination of the substances intended for removal is primarily used, the albumin loss is less than 5-10 g per treatment. An example of such a dialysis filter is constituted by the EMiC$^2$ filter produced by the company Fresenius Medical Care. The flow conditions at which such filters are operated in clinical use are selected appropriately for the blood flow 80-300 ml/min depending on use conditions: under the conditions of what is known as continuous veno-venous haemodialysis, blood flows of 60-80 ml/min are used, whereas in the case of dialysis unit-assisted intermittent haemodialysis, blood flows of 150-300 ml/min are used in acute cases, that is to say in patients with acute kidney failure, which also occurs very frequently in the case of sepsis. The dialysate flow is preferably set to 500 ml/min in the case of intermittent haemodialysis, whereas in the case of continuous veno-venous haemodialysis, dialysate flows in a ratio of 1:1 to the blood flow are conventional. The concentration of the lipopeptide/polymyxin in the dialysis fluid should lie in the range of 0.2-1.0 µg/l, that is to say should be slightly higher than the controlled serum concentration value of the patient to be treated, since the sieving coefficient of the aforementioned dialysis filter is between 0.8 (AF 1000) and 0.9 (EMiC$^2$), that is to say between 80 and 90%.

In practice, it is particularly expedient if the first or second carrier is a neutral, preferably synthetic polymer. A good reproducibility of the carrier material can thus be ensured. If it is a porous polymer, a good reproducibility in particular in terms of the porosity and particle size can then be ensured. The porosity and particle size can additionally vary very widely. The polymer may be both a homopolymer and a hetropolymer. These polymers are also known under the name "non-ionic macroreticular polymer resins" and for example are obtainable under the trade names "Amberchrom" and "Amberlite XAD" (Rohm&Haas/Dow Chemical Company).

For practical application, cross-linked polystyrene polymers and cross-linked ethylvinylbenzene polymers have proven to be particularly favourable. In the case of extracorporeal blood purification, high demands are placed on the sterility of the apparatus parts that come into contact with the bodily fluids of the patient. Cross-linked polystyrene polymers and cross-linked ethylvinylbenzene polymers are characterised by a high stability to heat and chemicals and are already established in clinical practice. In an advantageous variant, the cross-linked polystyrene polymer is a polystyrene divinylbenzene copolymer. In a further advantageous variant, the cross-linked ethylvinylbenzene polymer is an ethylvinylbenzene-divinylbenzene copolymer.

It is of course also possible, instead of the preferred polystyrene-divinylbenzene copolymer or ethylvinylbenzene-divinylbenzene copolymer, to use other neutral resins of high hydrophobicity which are well known to a person skilled in the relevant art. Representative examples for other neutral, hydrophobic polymers suitable for many embodiments of the invention include, for example, polymers from styrene and ethylvinylbenzene monomers cross-linked with trivinylcyclohexane, trivinylbenzene, divinylnaphthalene, divinyl sulfone, trimethylolpropane triacrylate, trimethylpropane trimethacrylate or resins based on aliphatic esters, and mixtures thereof.

The first or the second carrier is advantageously porous and has a mean particle size of 100 nm or smaller, preferably in a range from 1 to 100 nm. A particularly large inner surface is thus created for the depletion of undesirable components, such as cytokines, or for the adsorptive coating with endotoxin-binding lipopeptide.

Although a person skilled in the art is familiar with the meaning of the term "mean pore size" and the way in which the porosity or the mean pore size can be adjusted purposefully, this term will still be defined briefly at this juncture for reasons of clarity. The mean pore size relates to the mean diameter of the pores. With a Gaussian size distribution of the pore diameters of a porous material, the mean pore diameter is that corresponding to the maximum of the distribution curve. The mean pore diameter can be determined for example by means of nitrogen adsorption (as described in Weber et al. 2008; Neutral styrene divinylbenzene copolymers for adsorption of toxins in liver failure.

Biomacromolecules 9(4):1322-1328)) or by means of mercury intrusion. The pore size of a polymer is adjusted by varying the concentration of the involved monomers or co-monomers, the solvent or the modulator. The smaller the pores of the polymer are selected, the greater is the inner surface of the polymer that is available for the adsorption of molecules (in this case undesirable blood components such as cytokines and/or endotoxin-binding lipopeptides). The larger the pores, the better is the accessibility of the pores for larger molecules. A production method for a synthetic, hydrophobic polymer of defined pore size, as can be used for many embodiments of the invention, is described in the above-mentioned publication by Weber et al.

The production of such carriers by copolymerisation of monovinyl and polyvinyl aromatic monomers, carried out as suspension polymerisation, is also known from U.S. Pat. No. 4,382,124. The polyvinyl aromatic monomers are used as cross-linkers of the polymers. For example, styrene and/or ethylstyrene, preferably ethylstyrene, is/are used as monovinyl aromatic compounds. Divinylbenzene is preferably used as polyvinyl aromatic compound. The porosity is obtained by addition of porogens to the monomers, which are removed again following the polymerisation. The porogens may have hydrophobic or hydrophilic properties. Examples include toluene and xylene for hydrophobic porogens and C4-C10 alcohols for hydrophilic porogens. However, mixtures of these two porogens classes can also be used. The pore sizes of the polymer carriers can be varied within wide limits by the degree of cross-linking of the polymers, the type and quantity of the porogens and the reaction conditions during polymerisation. A person skilled in the relevant art will know which parameters to select in order to obtain a neutral, hydrophobic carrier of desirable pore size.

A special embodiment of the production of porous hydrophobic carriers is constituted by preferably post cross-linking styrene-divinylbenzene copolymers by "hyper cross-linking" (Davankov et al. J. Polymer Science, 47, 95-101 (1974). Examples of such carriers include the Hypersol-Macronet sorbents by the Purolite Company. Carriers with very large inner surface can thus be produced, which contain practically only micropores <2 nm.

Carriers with neutral, hydrophobic surface and variable mean pore size and particle size can be acquired for example from Rohm&Haas/Dow Chemical Company and are obtainable under the trade names "Amberchrom CG" and "Amberlite XAD". Fine-pore carriers with neutral, hydrophobic surface and a mean pore size of approximately 2.5 nm and smaller are obtainable from the company Purolite (for example Hypersol-Macronet MN270, polystyrene divinylbenzene polymer with a mean pore size of 2.5 nm (25 Å)).

The total porosity of a carrier having a mean pore size from 1 to 100 nm is preferably 0.3-0.8 $cm^3/g$ polymer. The inner surfaces (or total surfaces) preferably lie in a range from 100 to 1500 $m^2/g$.

The mean pore size of the first or of the second carrier advantageously lies in a range of 20 nm smaller, preferably 1 to 20 nm, or in a range from 80 to 100 nm, since in these specific pore size ranges an adsorption of protein C by the first carrier or the second carrier is much less pronounced than in a pore size range of greater than 20 nm and less than 80 nm. With pore sizes <20 nm, less protein C passes into the pores. The protein C adsorption by the carrier rises with increasing pore size and decreases again with pore sizes greater than 80 nm. Although the protein C binding can be lowered to a minimum with larger selected pore sizes (greater than 80 nm), it is favourable for clinical application if the mean pore size is selected so as to be no greater than 100 nm, since the inner surface of the carrier may otherwise become too small. Protein C, a vitamin K-dependent protein in the blood plasma, can pass through the filter used in accordance with many embodiments of the invention and consequently comes into contact with the first or second carrier arranged in the filtrate circuit. Protein C is an important regulator of the blood clotting process and has an anticoagulatory effect. It can be assumed that the adsorption of protein S is also much lower, since protein S (62 000 Da) has a similar relative molecular weight compared with the protein C (69 000 Da). The same considerations apply to coagulation factors of similar molecular weight, such as factor VII, factor IX and factor X.

The total porosity of a carrier having a mean pore size of 20 nm or less is preferably 0.4 to 0.8 $cm^3/g$ polymer. The inner surfaces (or total surfaces) preferably lie in a range from 300 to 1500 $m^2/g$.

The total porosity of a carrier having a mean pore size from 80 to 100 nm is preferably 0.4 to 0.8 $cm^3/g$ polymer. The inner surfaces (or total surfaces) preferably lie in a range from 100 to 500 $m^2/g$.

In further variants, the first and the second carrier may be fibre-like or may be in particle form. The first and the second carrier, however, are preferably in particle form. Carriers in particle form are easier to handle compared with fibrous carriers. In addition, the porosity of particles can be produced and adjusted more easily.

The mean particle size of polymer carriers can be adjusted during polymerisation in the known manner, for example by type and quantity of suspension stabiliser and geometry and rotational speed of the agitator. Hydrophobic carriers with neutral, hydrophobic surface and variable mean pore size and mean particle size can be acquired for example by Rohm/Haas/Dow Chemical Company and are obtainable under the trade names "Amberchrom CG" and "Amberlite XAD". Fine-pore carriers of variable mean pore size and mean particle size are produced for example by the company Purolite.

AC fibres from the company Mast Carbon (UK) constitute examples for a suitable fibre-like carrier.

The first or the second carrier preferably has the form of microparticles having a mean particle size of 300 µm or smaller, preferably 2 to 300 µm. With larger particle sizes from this range, improved blood compatibility is provided by the smaller outer surface, whereas smaller particles are characterised by higher dynamic efficacy.

In a particularly preferred embodiment, the first carrier has a mean pore size from 10 to 20 nm or a mean pore size from 80 to 100 nm and an mean particle size from 75 to 150 µm. it has been found that this particle size range is advantageous in terms of the undesirable adsorption of protein C (see example 8 below). Coagulation complications (venous thromboses, pulmonary embolisms), which are caused by an undesirable protein C adsorption, can thus be minimised. With a particle size from 75 to 150 µm, the outer surface of the carrier still appears to be small enough to bind protein C to an insignificant extent, if at all; however, it is clearly still large enough to keep small the diffusion paths for the substances to be adsorbed. In this preferred embodiment, the particle size is at least 75 µm, since physiologically relevant quantities of protein C still remain here in the blood or blood plasma, even after relatively long incubation. In an advantageous sub-variant, the first carrier has a mean pore size from 10 to 20 nm and a mean particle size from 75 to 150 µm. With a mean pore size of less than 10 nm, the adsorption efficiency for the inflammation mediators to be removed, such as cytokines, in particular TNF-α, decreases again. With a pore size of more than 20 nm, the inner surface is smaller and the adsorption capacity for cytokines decreases. This embodiment of the perfusion apparatus according to the invention inclusive of the advantageous sub-variants described hereinafter is therefore extraordinarily well suited for the treatment of sepsis, in particular septic shock, and sepsis-like states.

In a particularly advantageous and preferred sub-variant of this embodiment, the first carrier has a mean pore size from 10 to 20 nm or a mean pore size from 80 to 100 nm, preferably a mean pore size from 10 to 20 nm and a mean particle size from 75 to 150 µm, wherein the surface of the first carrier has an adsorptive coating formed of the endotoxin-binding lipopeptide, that is to say in this sub-variant the depletion agent also acts, as described above in detail with reference to the first embodiment, as a dispensing means for the endotoxin-binding lipopeptide (see also FIGS. 1 and 2 further below). As already mentioned, it has been found in laboratory tests that the adsorptive coating of the carrier surface of the lipopeptide has no disadvantageous effects on the adsorption of the cytokines. In embodiments in which a second carrier is provided (see above or the comments below with regard to FIG. 5), it is advantageous in accordance with a further sub-variant if the second carrier has a pore size of 20 nm or smaller.

Since the protein C adsorption decreases with rising mean particle size, the first carrier in a further advantageous sub-variant has a mean particle size from 100 to 150 µm. The carrier more preferably has a mean particle size from 110 to 130 µm, ideally a mean particle size of approximately 120 µm, since at these particle sizes on the one hand toxic substances, such as cytokines, and on the other hand important coagulation factors, such as protein C, can hardly continue to be adsorbed, even if the bodily fluid (blood plasma) is brought into contact with the first carrier over a relatively long period of time.

In a variant of the extracorporeal perfusion apparatus, the filtrate circuit leads into the extracorporeal blood circuit at a position downstream of the filter. In this variant the filtrate circuit is open and the fractionated plasma is fed directly to the extracorporeal blood circuit downstream of the filter by passing through the filtrate circuit (see schematic illustration of this variant in FIGS. 1, 3, 5 and 7). The basic principle of this variant is currently used in immunoadsorption (for example apheresis apparatuses from the company AsahiKasei, Japan). The depletion agent or the dispensing means (first or second carrier) is preferably arranged in this variant in a device which is arranged in the filtrate circuit and through which blood plasma can flow and which for example can be formed as a column or cartridge.

In another variant of the extracorporeal blood circuit, the filtrate circuit is closed and the fractionated plasma passes via the membrane of the filter back into the blood flowing in the extracorporeal blood circuit (see schematic illustration of this variant in FIGS. 2, 4 and 6). The basic principle of the second variant is known by the blood purification system Prometheus® (Fresenius Medical Care GmbH, Germany) [Falkenhagen D, Strobl W, Vogt G, Schrefl A, Linsberger I, Gerner F J, Schoenhofen M.: Fractionated plasma separation and adsorption system: a novel system for blood purification to remove albumin bound substances. Artif Organs. 1999 January; 23(1):81-6].). The depletion agent or the dispensing means (first or second carrier) can be arranged in a device which is arranged in the filtrate circuit and through which blood plasma can flow and which for example can be formed as a column or cartridge.

In an advantageous embodiment the filtrate circuit leads into the filter and thus forms a circuit that is closed in the filtrate region, wherein the first carrier has the form of microparticles and the filtrate circuit comprises a suspension of these microparticles, wherein the microparticles have a mean particle size of 20 µm or smaller, preferably a mean particle size of 8 µm or smaller, ideally a mean particle size of 5 µm or smaller. This embodiment is a development of the above-mentioned embodiments, in which only the first carrier (with or without an adsorptive coating with endotoxin-binding lipopeptide) is arranged in the filtrate circuit. The microparticle-shaped first carrier (with or without lipopeptide coating) circulates here as a suspension in the filtrate circuit. Due to the particle sizes selected so as to be very small, the risk of a pulmonary embolism can be avoided, should the microparticles pass for example by means of a filter leak into the extracorporeal blood circuit and then into the body of the patient. An extracorporeal plasma circuit, in which a suspension of microparticles is contained, constitutes a key component of a microspheres-based detoxification system (MDS) and has already been described in EP 0776223 B and U.S. Pat. No. 5,855,782.

Many embodiments of the invention are advantageously used for the treatment of an infection with gram-negative bacteria, in particular for the prophylaxis or treatment of a systemic inflammatory reaction (SIRS), sepsis, severe sepsis or septic shock. Representative examples for disease patterns that can be treated by means of the perfusion apparatus according to many embodiments of the invention are those that occur following an infection with gram-negative bacteria and may then lead to SIRS, sepsis, severe sepsis with multi-organ failure, or septic shock.

Representative examples for gram-negative bacteria include *Escherichia* spp, *Haemophilus influenzae, Pseudomonas aeruginosa, Pasteurella, Enterobacter* spp., *Salmonella* spp. and *Shigella* spp. Many embodiments of the invention are particularly advantageous in the case of gram-negative bacteria for which an increased occurrence of multi-resistant strains has been observed, wherein *Pseudomonas aeruginosa* is to be highlighted here as a particularly relevant example.

As already mentioned above, an increased endotoxin distribution occurs or may occur with the use of antibiotics in the case of an infection with gram-negative bacteria and as a result of the cell lysis induced by the administration of antibiotics. An increased endotoxin distribution has been described for example for antibiotics that preferably bind to PBP-3 (penicillin-binding protein-3), for example the most commonly used antibiotics in the group of cephalosporins, such as ceftazidime. Many embodiments of the invention are therefore used advantageously as an additional therapeutic or prophylactic measure in the scope of conventional treatment of bacterial infections by means of antibiotics in order to resist endotoxin distribution induced by the administration of antibiotics and induction of cytokines.

In a further aspect, many embodiments are advantageously used for the prophylaxis or treatment of an inflammatory reaction as a result of acute liver failure or acute decompensation in the case of chronic liver failure, in particular a systemic inflammatory reaction (SIRS), sepsis, severe sepsis with multi-organ failure, or septic shock. In patients with intact liver functions, the endotoxins passing from the intestine into the bloodstream are eliminated from the reticuloendothelial system (RES) or Kupffer cells by endocytosis. Acute decompensation may occur in patients with chronic liver failure. In this case, endotoxins of the normal intestinal flora pass the intestinal barrier and therefore pass unimpeded into the liver and lead to a systemic inflammatory reaction (SIRS), sepsis, severe sepsis with multi-organ failure, or septic shock.

Many embodiments also relate to a method for the prophylaxis or treatment of conditions and states caused by endotoxemia by means of an extracorporeal perfusion apparatus according to some embodiments of the invention. The above-specified definitions and developments are to be applied equally to the method.

Prior to starting the treatment of the patient by means of the perfusion apparatus according to several embodiments of the invention, a bolus is preferably administered once in order to quickly break down and adjust a lipopeptide serum concentration from preferably 0.01 µg/ml to 0.8 µg/ml. Within the scope of this disclosure, the term "bolus" is thus understood to mean a one-time parenteral administration of the endotoxin-binding lipopeptide in the form of the preparation, preferably in the form of an injection or infusion preparation. The bolus administration can be used advantageously in conjunction with all above-mentioned embodiments of the apparatus according to the invention. Examples for injection solutions for the bolus administration are specified below in Example 4.

BRIEF DESCRIPTION OF THE FIGURES

Numerous embodiments of the invention will be explained hereinafter in greater detail on the basis of non-limiting examples and drawings. In the drawings.

DETAILED DESCRIPTION OF THE INVENTION

Figure 1:
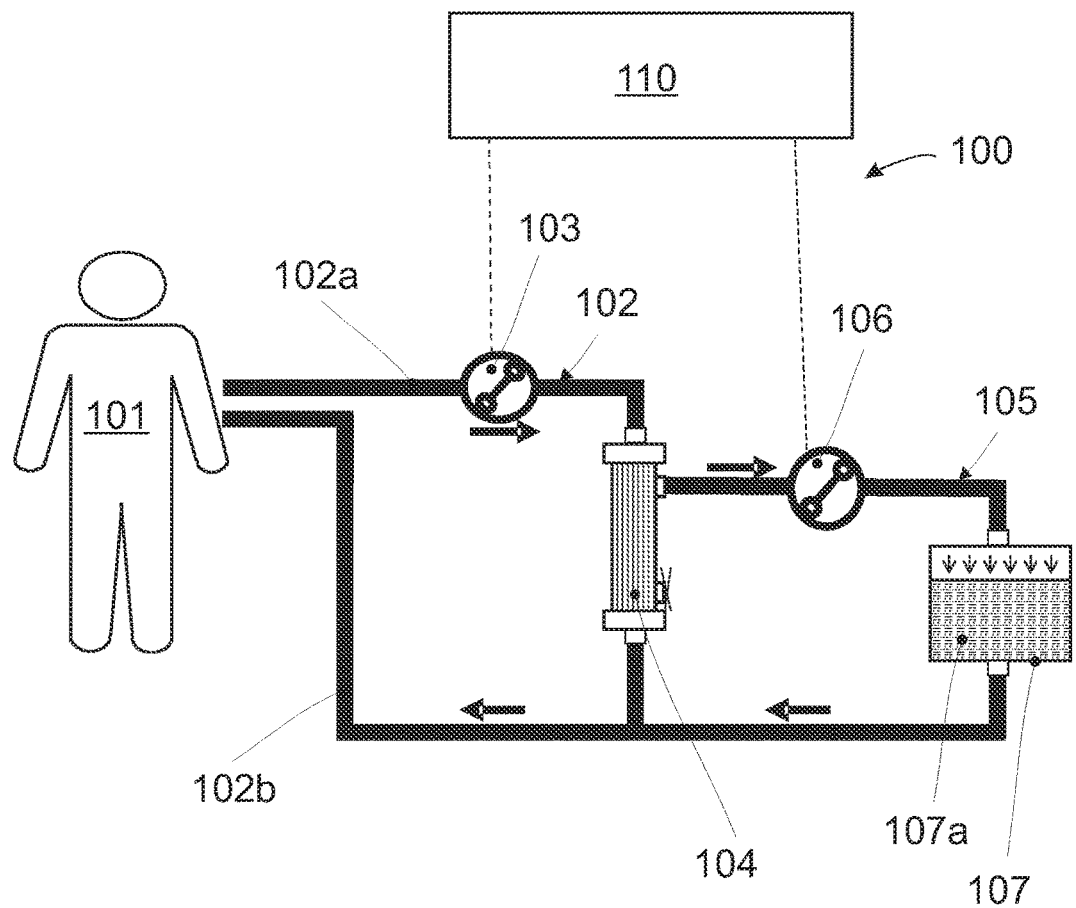
FIG. 1 shows a schematic illustration of an embodiment of an extracorporeal perfusion apparatus according to an embodiment of the invention with open filtrate circuit, wherein the depletion agent arranged in the filtrate circuit also acts simultaneously as dispensing means for polymyxin B.

FIG. 1 shows a schematic illustration of an extracorporeal perfusion apparatus 100 (extracorporeal blood purification apparatus 100). The perfusion apparatus 100 has an extracorporeal blood circuit 102 with an arterial inflow 102a (arterial branch) from a patient 101 to a filter 104 and a venous outflow 102b (venous branch) from the filter 104 to the patient 101. The patient's blood is conveyed in the blood circuit 102 by means of a blood pump 103 (pump rate $Q_{Blut}$=60-300 ml/min depending on treatment method). The filter 104 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the filter 104 and fed to a filtrate circuit 105. A filter with a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 105 is formed as an open circuit, which leads downstream of the filter 104 into the venous branch 102b. The fractionated blood plasma is conveyed through the filtrate circuit 105 by means of a filtrate pump 106 (pump rate $Q_{frakt.\ Plasma}$=15-20% of $Q_{Blut}$.). The perfusion apparatus 100 is also assigned a controller 110 for the automated control of the apparatus 100, said controller also being connected to the pumps 103, 106 via signal connections. The controller 110 is usefully also configured for central data acquisition and data output.

The fractionated plasma conveyed through the filtrate circuit 105 is guided through a column 107 arranged in the filtrate circuit 105. The column 107 contains an adsorber bed 107a formed of a carrier having a neutral, hydrophobic surface, wherein the carrier surface has an adsorptive coating formed of lipopeptide molecules, here polymyxin. In FIG. 1, the carrier is a polystyrene divinylbenzene polymer with a mean particle size of 120 m and a mean pore size from 15 to 20 nm, wherein the surface of the polymer has an adsorptive coating with polymyxin (production of a polymer coated with polymyxin, see example 1). The adsorber bed 107a therefore functions on the one hand as a depletion agent for cytokines such as TNF-α, IL-6 and IL-10, since these are adsorbed at the carrier and are removed from the plasma. On the other hand, the adsorber bed 107a also acts as a dispensing means for continuously dispensing polymyxin into the blood plasma by continuously dispensing a very small quantity of polymyxin into the fractionated blood plasma conveyed in the filtrate circuit 105 (desorption). The polymyxin passes on from there into the venous outflow 102b of the extracorporeal blood circuit 102, where it forms a complex with the endotoxins present in the blood and makes these harmless.

Figure 2:
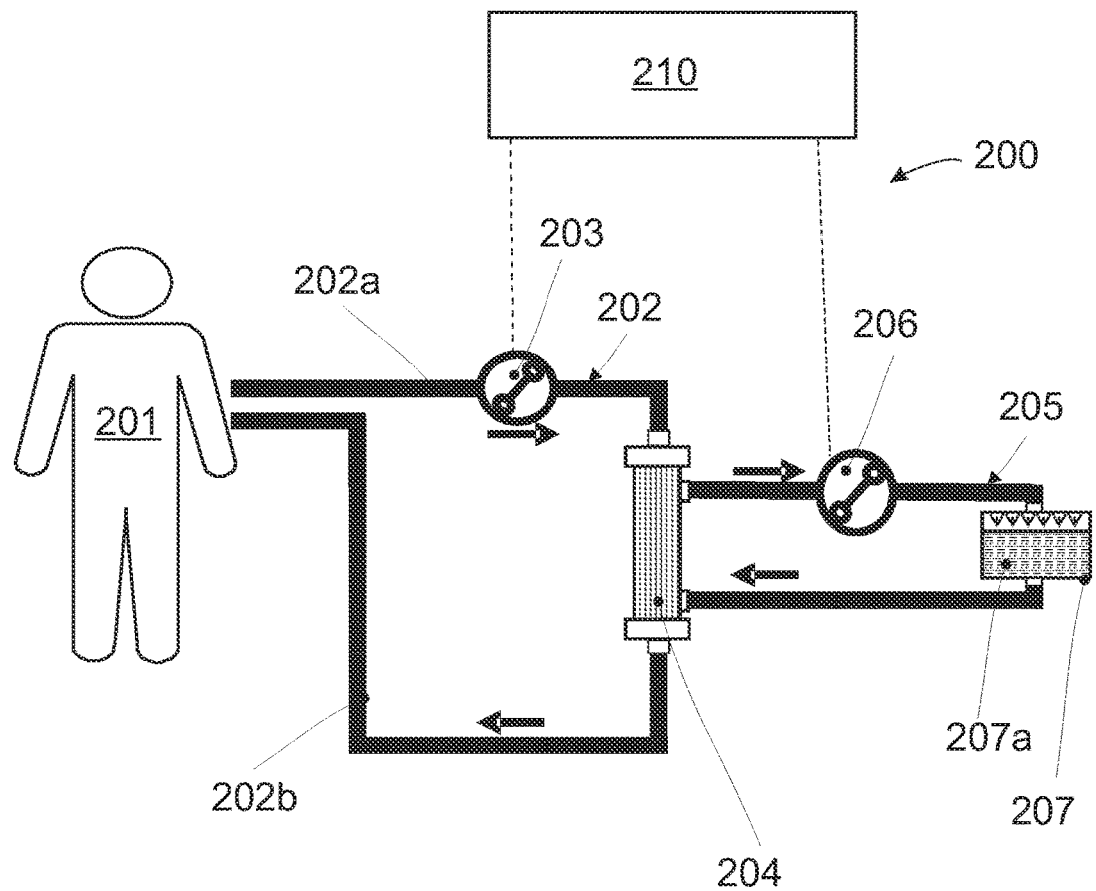
FIG. 2 shows a schematic illustration of a further embodiment of an extracorporeal perfusion apparatus according to an embodiment of the invention with closed filtrate circuit, wherein the depletion agent arranged in the filtrate circuit also acts simultaneously as dispensing means for polymyxin.

FIG. 2 shows a schematic illustration of an extracorporeal perfusion apparatus 200 (extracorporeal blood purification device 200). The perfusion apparatus 200 has an extracorporeal blood circuit 202 with an arterial inflow 202a (arterial branch) from a patient 201 to a filter 204 and a venous outflow 202b (venous branch) from the filter 204 to the patient 201. The patient's blood is conveyed in the blood circuit 202 by means of a blood pump 203 (pump rate $Q_{Blut}$=30-70 ml/min). The filter 204 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the plasma filter 204 and is fed to a filtrate circuit 205. A filter having a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 205 is formed as a circuit that is closed in the filtrate region, wherein the fractionated blood plasma is conveyed thorough the filtrate circuit 205 by means of a filtrate pump 206 (pump rate $Q_{frakt.\ Plasma}$=15-25% of $Q_{Blut}$). The perfusion apparatus 200 is also assigned a controller 210 for the automated control of the apparatus 200, said controller also being connected to the pumps 203, 206 via signal connections. The controller 210 is usefully also configured for central data acquisition and for data output.

The fractionated plasma conveyed through the filtrate circuit 205 is guided through a column 207 arranged in the filtrate circuit 205. The column 207 contains an adsorber bed 207a formed of a carrier having a neutral, hydrophobic surface, wherein the carrier surface has an adsorptive coating formed of lipopeptide molecules, here polymyxin. In FIG. 2, the carrier is a polystyrene divinylbenzene polymer with a mean particle size of 120 μm and a mean pore size from 15 to 20 nm, wherein the surface of the polymer has an adsorptive coating with polymyxin (production of a polymer coated with polymyxin, see example 1). The adsorber bed 207a therefore functions on the one hand as a depletion agent for cytokines such as TNF-α, IL-6, IL-10, since these are adsorbed at the carrier and are removed from the plasma. On the other hand, the adsorber bed 207a also acts as a dispensing means for continuously dispensing polymyxin into the blood plasma by continuously dispensing a very small quantity of polymyxin into the fractionated blood plasma conveyed in the filtrate circuit 205 (desorption). The polymyxin passes on from there into extracorporeal blood circuit 202. The polymyxin molecules then form a complex with the endotoxins present in the blood.

Figure 3:
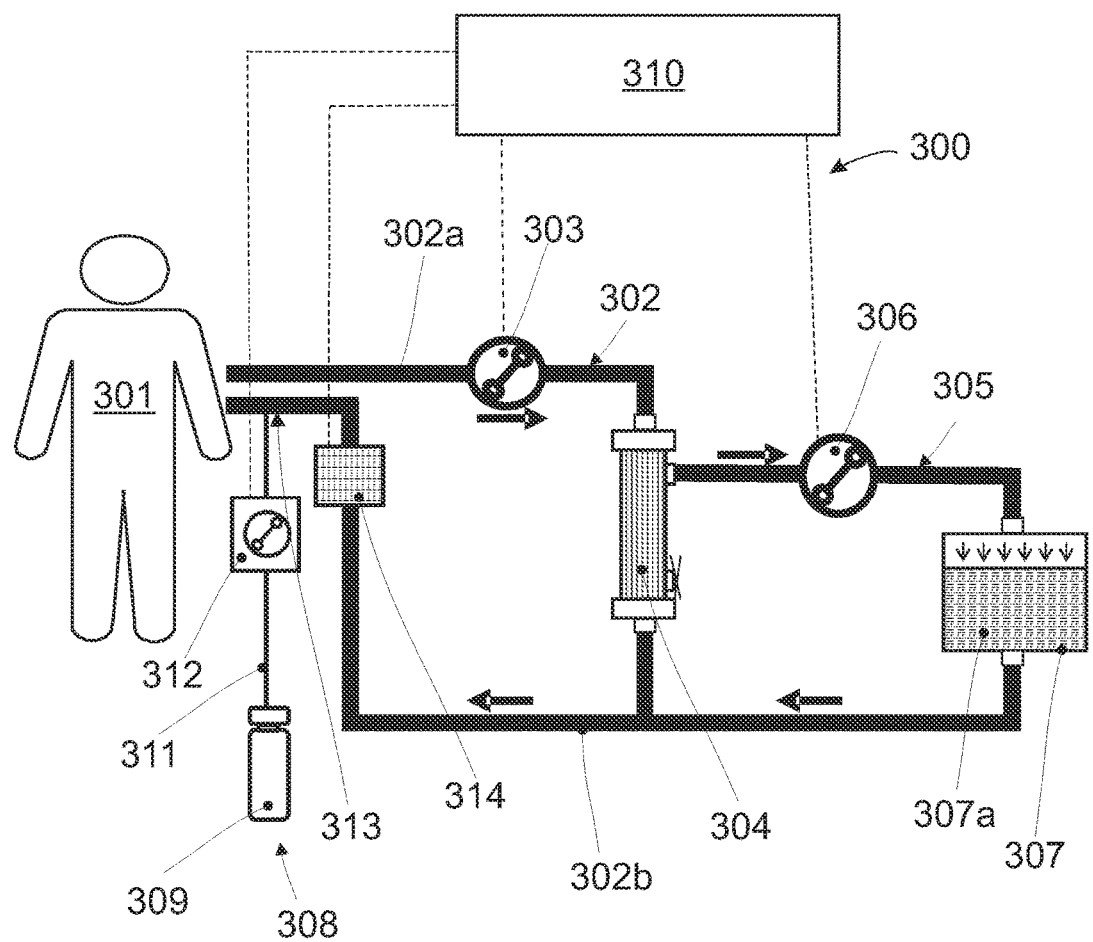
FIG. 3 shows a schematic illustration of a further embodiment of an extracorporeal perfusion apparatus according to an embodiment of the invention with open filtrate circuit and a dosing device for polymyxin.

FIG. 3 shows a schematic illustration of an extracorporeal perfusion apparatus 300 (extracorporeal blood purification apparatus 300). The perfusion apparatus 300 has an extracorporeal blood circuit 302 with an arterial inflow 302a (arterial branch) from a patient 301 to a filter 304 and a venous outflow 302b (venous branch) from the filter 304 to the patient 301. The patient's blood is conveyed in the blood circuit 302 by means of a blood pump 303 (pump rate $Q_{Blut}$=60-300 ml/min). The filter 304 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the filter 304 and fed to a filtrate circuit 305. A filter with a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 305 is formed as an open circuit, which leads downstream of the filter 304 into the venous branch 302b. The fractionated blood plasma is conveyed through the filtrate circuit 305 by means of a filtrate pump 306 (pump rate $Q_{frakt.\ Plasma}$=15-25% of $Q_{Blut}$).

The fractionated plasma conveyed through the filtrate circuit 305 is guided through a column 307 arranged in the filtrate circuit 305. The column 307 contains an adsorber bed 307a formed of a carrier with a neutral, hydrophobic surface. In FIG. 3 the carrier is a polystyrene divinylbenzene polymer with a mean particle size of 120 μm and a mean pore size from 15 to 20 nm. The adsorber bed 307a functions as a depletion agent for cytokines, such as TNF-αc, IL-6 and IL-10, by adsorbing these at the carrier and removing them from the plasma.

In order to dispense an endotoxin-binding lipopeptide, the perfusion apparatus 300 is assigned an infusion device 308 known per se comprising an infusion container 309 (for example infusion bottle or infusion bag) containing a lipopeptide infusion solution, here a polymyxin infusion solution, an infusion tube 311 and an infusion pump 312.

Suitable infusion solutions are described further below in Example 5. The polymyxin is infused at a lipopeptide feed point 313 into the venous outflow 302b of the extracorporeal blood circuit 302. The polymyxin molecules then form a complex with the endotoxins present in the blood.

FIG. 3 also shows an advantageous development, in which a polymyxin sensor 314 is arranged downstream of the filter 304 and upstream of the lipopeptide feed point 313. By way of example, a polymyxin sensor as described previously by Jiang et al. (Jiang et al. 2004. A synthetic peptide derived from bactericidal/permeability-increasing protein neutralizes endotoxin in vitro and in vivo. International Immunopharmacology 4:527-537) can be used for this purpose. For the measurement, a small quantity of blood is preferably conveyed from the extracorporeal blood circuit 302 via a branch line to the sensor 314 and is rejected once the concentration of the polymyxin has been determined. The perfusion apparatus 300 is also assigned a controller 310 for the automated control of the apparatus 300, said controller also being connected to the pumps 303, 306, 311 and where applicable to the polymyxin sensor 314 via signal connections. The controller 310 is expediently also configured for central data acquisition and for data output. The perfusion apparatus 300 may also be assigned a control circuit controlled by means of the controller 310, wherein, by actuating the infusion pump 312, the infused quantity of polymyxin is controlled with respect to a predefined target value or target value range depending on the polymyxin current value (polymyxin serum concentration) measured by the sensor 314. The target value or target value range of the polymyxin serum concentration is typically in a range from 0.01-0.8 µg/ml.

Figure 4:
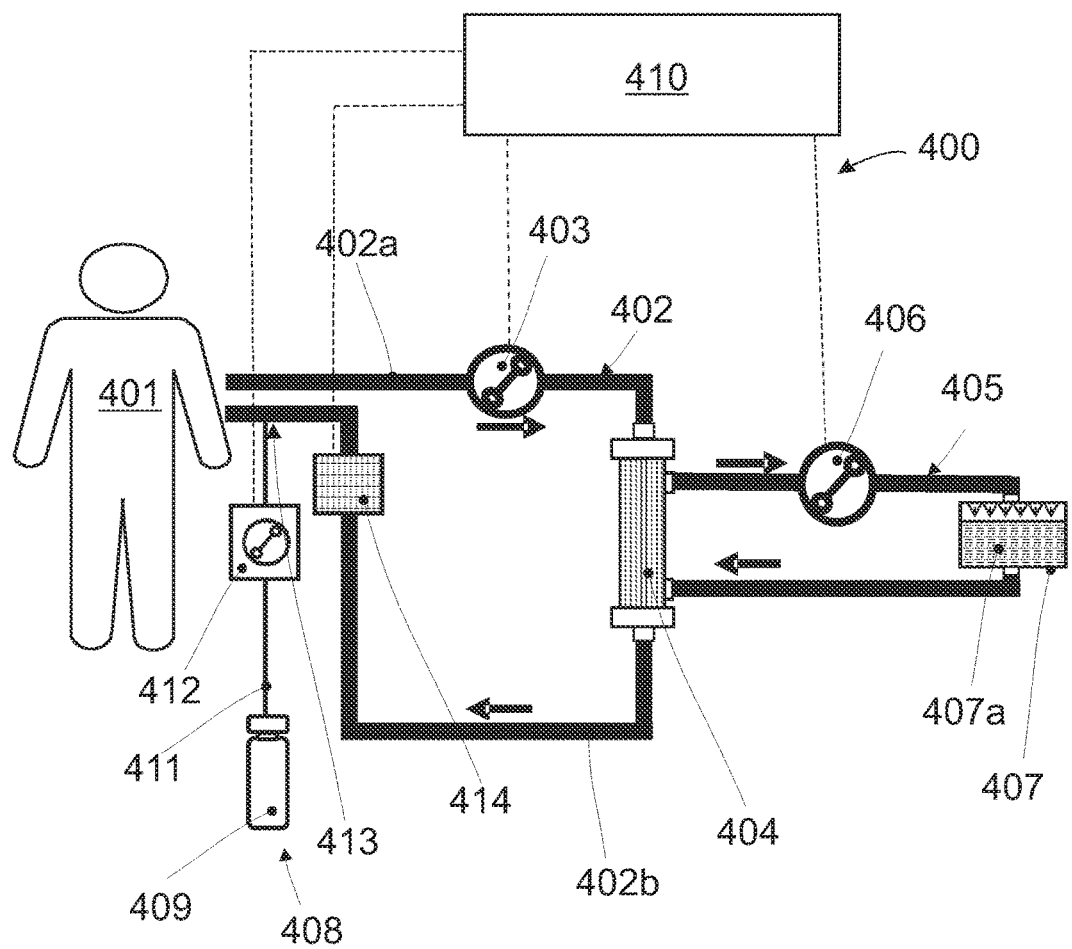
FIG. 4 shows a schematic illustration of two further embodiments of an extracorporeal perfusion apparatus according to an embodiment of the invention with closed filtrate circuit and a dosing device for polymyxin.

FIG. 4 shows a schematic illustration of an extracorporeal perfusion apparatus 400 (extracorporeal blood purification device 400). The perfusion apparatus 400 has an extracorporeal blood circuit 402 with an arterial inflow 402a (arterial branch) from a patient 401 to a filter 404 and a venous outflow 402b (venous branch) from the filter 404 to the patient 401. The patient's blood is conveyed in the blood circuit 402 by means of a blood pump 403 (pump rate $Q_{Blut}$=60-300 ml/min). The filter 404 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the filter 404 and is fed to a filtrate circuit 405. A filter having a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 405 is formed as a circuit that is closed in the filtrate region, wherein the fractionated blood plasma is conveyed thorough the filtrate circuit 405 by means of a filtrate pump 406 (pump rate $Q_{frakt.\ Plasma}$=15-25% of $Q_{Blut}$).

The fractionated plasma conveyed through the filtrate circuit 405 is guided through a column 407 arranged in the filtrate circuit 405. The column 407 contains an adsorber bed 407a formed of a carrier having a neutral, hydrophobic surface. In FIG. 4, the carrier is a polystyrene divinylbenzene polymer with a mean particle size of 120 µm and a mean pore size from 15 to 20 nm. The adsorber bed 407a acts as a depletion agent for cytokines such as TNF-α, IL-6 and IL-10, by adsorbing these at the carrier and removing them from the plasma.

In order to dispense an endotoxin-binding lipopeptide, the perfusion apparatus 400 is an infusion device 408 known per se comprising an infusion container 409 (for example infusion bottle or infusion bag) containing a lipopeptide infusion solution, here a polymyxin infusion solution, an infusion tube 411 and an infusion pump 412. Suitable infusion solutions are described further below in Example 5. The polymyxin is infused at a lipopeptide feed point 413 into the venous outflow 402b of the extracorporeal blood circuit 402. The polymyxin molecules then form a complex with the endotoxins present in the blood.

Similarly to FIG. 3, FIG. 4 further shows an advantageous development, in which a polymyxin sensor 414 is arranged downstream of the filter 404 and upstream of the lipopeptide feed point 413. By way of example, a polymyxin sensor as described previously by Jiang et al. (Jiang et al. 2004. A synthetic peptide derived from bactericidal/permeability-increasing protein neutralizes endotoxin in vitro and in vivo. International Immunopharmacology 4:527-537) can be used for this purpose. For the measurement, a small quantity of blood is preferably conveyed from the extracorporeal blood circuit 402 via a branch line to the sensor 414 and is rejected once the concentration of the polymyxin has been determined. The perfusion apparatus 400 is also assigned a controller 410 for the automated control of the apparatus 400, said controller also being connected to the pumps 403, 406, 411 and where applicable to the polymyxin sensor 414 via signal connections. The controller 410 is expediently also configured for central data acquisition and for data output. The perfusion apparatus 400 may also be assigned a control circuit controlled by means of the controller 410, wherein, by actuating the infusion pump 412, the infused quantity of polymyxin is controlled with respect to a predefined target value or target value range depending on the polymyxin current value (polymyxin serum concentration) measured by the sensor 414. The target value or target value range of the polymyxin serum concentration is typically in a range from 0.01-0.8 µg/ml.

Figure 5:
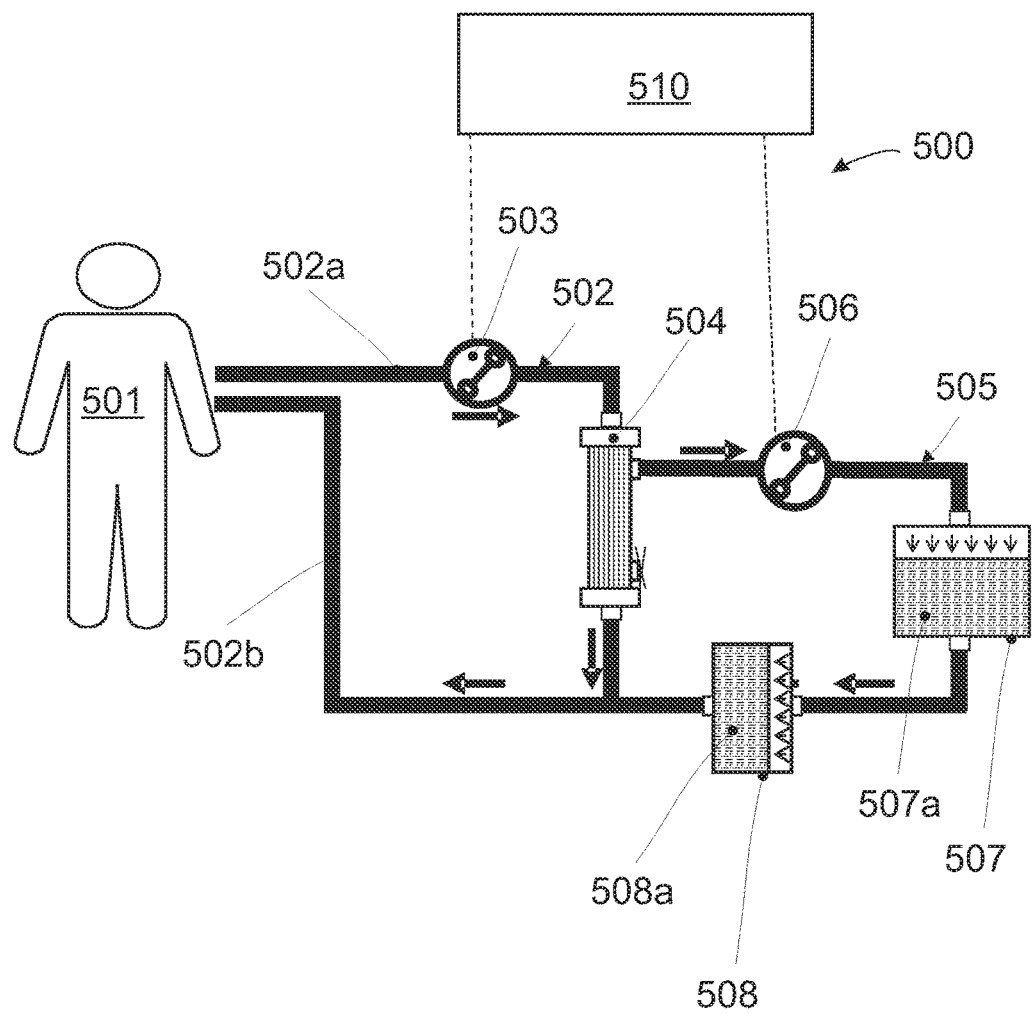
FIG. 5 shows a schematic illustration of a further embodiment of an extracorporeal perfusion apparatus according to an embodiment of the invention with open filtrate circuit, wherein the dispensing means for polymyxin is arranged downstream of the depletion agent in the filtrate circuit.

FIG. 5 shows a schematic illustration of an extracorporeal perfusion apparatus 500 (extracorporeal blood purification device 500). The perfusion apparatus 500 has an extracorporeal blood circuit 502 with an arterial inflow 502a (arterial branch) from a patient 501 to a filter 504 and a venous outflow 502b (venous branch) from the filter 504 to the patient 501. The patient's blood is conveyed in the blood circuit 502 by means of a blood pump 503 (pump rate $Q_{Blut}$=60-300 ml/min). The filter 504 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the filter 504 and is fed to a filtrate circuit 505. A filter having a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 505 is formed as an open circuit, which leads downstream of the filter 504 into the venous branch 502. The fractionated blood plasma is conveyed thorough the filtrate circuit 505 by means of a filtrate pump 506 (pump rate $Q_{frakt.\ Plasma}$=15-

25% of $Q_{Blut}$). The perfusion apparatus 500 is also assigned a controller 510 for the automated control of the apparatus 500, said controller also being connected to the pumps 503, 506 via signal connections. The controller 510 is usefully also configured for central data acquisition and for data output. In FIG. 5 the filtrate circuit 505 is formed as an open circuit. However, the filtrate circuit 505 can also be formed as a closed circuit.

The fractionated plasma conveyed through the filtrate circuit 505 is guided through a column 507 arranged in the filtrate circuit 505. The column 507 contains an adsorber bed 507a formed of a carrier with a neutral, hydrophobic surface. In FIG. 5 the carrier is a polystyrene divinylbenzene polymer with a mean particle size of 120 m and a mean pore size from 15 to 20 nm. The adsorber bed 507a functions as a depletion agent for cytokines, such as TNF-α, IL-6 and IL-10, by adsorbing these at the carrier and removing them from the plasma.

In order to dispense a lipopeptide, a further column 508 is arranged in the filtrated circuit 505, downstream of the column 507. The column 508 contains a carrier bed 508a formed of a carrier having a neutral, hydrophobic surface, wherein the carrier surface has an adsorptive coating formed of lipopeptide molecules, here polymyxin. In FIG. 5 the carrier is a polystyrene divinylbenzene polymer with a mean particle size of 120 μm and a mean pore size from 15 to 20 nm, wherein the surface of the polymer has an adsorptive coating with polymyxin (production of a polymer coated with polymyxin, see Example 1). The carrier bed 508a acts a dispensing means for continuously dispensing polymyxin into the blood plasma by continuously dispensing a very small quantity of polymyxin into the fractionated blood plasma conveyed in the filtrate circuit 505 (desorption). From there, the polymyxin passes on into the extracorporeal blood circuit 502. The polymyxin molecules then form a complex with the endotoxins present in the blood.

Figure 6:
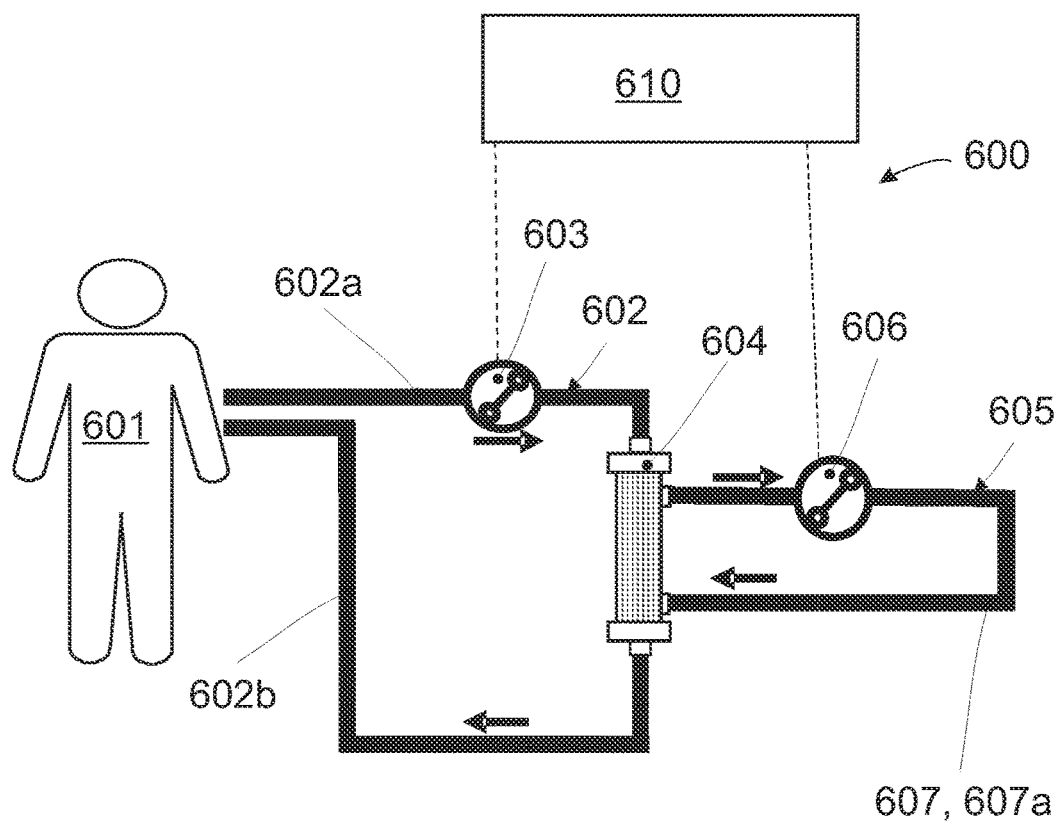
FIG. 6 shows a schematic illustration of a further embodiment of an extracorporeal perfusion apparatus according to an embodiment of the invention with closed filtrate circuit, wherein the dispensing means for polymyxin is present in the filtrate circuit as microparticle suspension.

FIG. 6 shows a schematic illustration of an extracorporeal perfusion apparatus 600 (extracorporeal blood purification device 600). The perfusion apparatus 600 has an extracorporeal blood circuit 602 with an arterial inflow 602a (arterial branch) from a patient 601 to a filter 604 and a venous outflow 602b (venous branch) from the filter 604 to the patient 601. The patient's blood is conveyed in the blood circuit 602 by means of a blood pump 603 (pump rate $Q_{Blut}$=60-300 ml/min). The filter 604 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the filter 604 and is fed to a filtrate circuit 605. A filter having a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 605 is formed as a circuit that is closed in the filtrate region, wherein the fractionated blood plasma is conveyed thorough the filtrate circuit 605 by means of a filtrate pump 606 (pump rate $Q_{frakt.\ Plasma}$=15-25% of $Q_{Blut}$).

The perfusion apparatus 600 is also assigned a controller 610 for the automated control of the apparatus 600, said controller also being connected to the pumps 603, 606 via signal connections. The controller 610 is expediently also configured for central data acquisition and data output.

Here, the filtrate circuit 605, as depletion agent/dispensing means 607, comprises a suspension (not illustrated in detail) of the carrier 607a, that is to say the depletion agent/dispensing means 607 or the carrier 607a is in microparticle form and is present as suspension distributed in the fractionated plasma and circulates as suspension in the filtrate circuit 605. The carrier 607a in microparticle form has a neutral, hydrophobic surface, wherein the carrier surface has an adsorptive coating formed of lipopeptide molecules, here polymyxin. In FIG. 6, the carrier 607a is a polystyrene divinylbenzene polymer with a mean particle size of 5 m+/−3-4 μm and a mean pore size of 15 to 20 nm (source of polymer acquisition: Rohm&Haas), wherein the surface of the polymer has an adsorptive coating with polymyxin (production of a polymer coated with polymyxin, see example 1). The carrier 607a in microparticle form thus functions on the one hand as a depletion agent for cytokines, such as TNF-α, IL-6 and IL-10, by adsorbing these at the carrier and removing them from the plasma. On the other hand, the carrier 607a in microparticle form also acts as a dispensing means for continuously dispensing polymyxin into the blood plasma by continuously dispensing a very small quantity of polymyxin into the fractionated blood plasma conveyed in the filtrate circuit 605 (desorption). From there, the polymyxin passes on into the extracorporeal blood circuit 602. The polymyxin molecules then form a complex with the endotoxins present in the blood.

Figure 7:
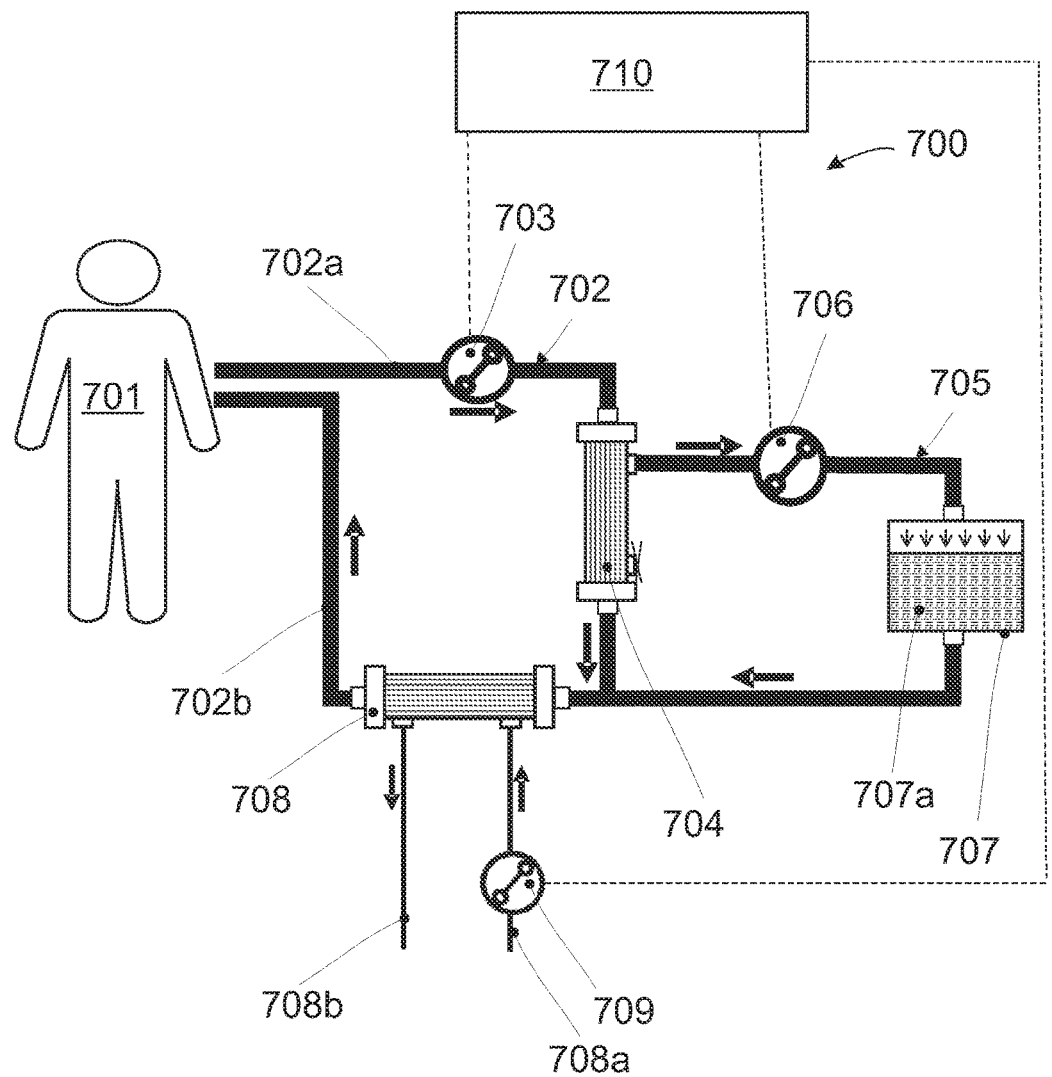
FIG. 7 shows a schematic illustration of a further embodiment of an extracorporeal perfusion apparatus according to an embodiment of the invention with open filtrate circuit and a dialyser for dispensing polymyxin arranged downstream of the filter in the extracorporeal blood circuit.

FIG. 7 shows a schematic illustration of an extracorporeal perfusion apparatus 700 (extracorporeal blood purification device 700). The perfusion apparatus 700 has an extracorporeal blood circuit 702 with an arterial inflow 702a (arterial branch) from a patient 701 to a filter 704 and a venous outflow 702b (venous branch) from the filter 704 to the patient 701. The patient's blood is conveyed in the blood circuit 702 by means of a blood pump 703 (pump rate $Q_{Blut}$=60-300 ml/min). The filter 704 has a sieving coefficient of 5% for substances with a molar mass of 340 000 g/mol (340 kDa), here a filter of the Albuflow® type (manufacturer: Fresenius Medical Care; material: polysulfone hollow fibres; sieving coefficient for albumin of ≥0.6 and for fibrinogen ≤0.1). Some of the blood plasma (=fractionated plasma) is filtered off by the filter 704 and is fed to a filtrate circuit 705. A filter having a sieving coefficient of 5% for substances with a relative molar mass of 340 kDa allows fractionated plasma to pass through, such that high-molecular blood plasma components such as fibrinogen, immunoglobulins, LDL, HDL, etc. are retained, whereas smaller blood components such as albumin or protein C pass through the filter membrane. The filtrate circuit 705 is formed as an open circuit, which leads downstream of the filter 704 into the venous branch 702b. The fractionated blood plasma is conveyed thorough the filtrate circuit 705 by means of a filtrate pump 706 (pump rate $Q_{frakt.\ Plasma}$=15-25% of $Q_{Blut}$). In FIG. 7 the filtrate circuit 705 is formed as an open circuit. However, the filtrate circuit 705 can also be formed as a closed circuit.

The fractionated plasma conveyed through the filtrate circuit 705 is guided through a column 707 arranged in the filtrate circuit 705. The column 707 contains an adsorber bed 707a formed of a carrier with a neutral, hydrophobic surface. In FIG. 7 the carrier is a polystyrene divinylbenzene polymer with a mean particle size of 120 μm and a mean pore size from 15 to 20 nm. The adsorber bed 707a functions as a depletion agent for cytokines, such as TNF-α, IL-6 and IL-10, by adsorbing these at the carrier and removing them from the plasma.

In order to dispense a lipopeptide, a dialyser 708 (dialysis filter 708) is arranged in the venous branch 702b of the extracorporeal blood circuit 702. In the dialyser, the blood is brought into contact with the dialysis solution via a semipermeable membrane. The dialysis solution is pumped by means of a dialysis solution pump 709 into the dialyser 708 via a dialysis solution inflow 708a. After having passed through the dialyser 708, the dialysate is removed and disposed of via a dialysate outflow 708b. The lipopeptide, here polymyxin, is fed to the blood by means of the dialysis solution. In the embodiment illustrated in FIG. 7, the dialyser 708 thus acts as dispensing means for dispensing the lipopeptide (polymyxin) into the extracorporeal blood circuit 702. The polymyxin molecules then form a complex with the endotoxins present in the blood.

The dialyser 708 preferably comprises a hydrophilic polysulfone membrane with a surface of 1.4-2.0 $m^2$, which has been produced by blending with PVP (polyvinylpyrrolidone). By way of example, these membranes are used in the filters from the company Fresenius Medical Care in models AF 1000 and FX60, inter alia. These dialysis filters have a sieving coefficient for albumin less than 0.1%. The use of what is known as a high cut-off filter, which is also based on the use of hydrophilic polysulfone membranes having a sieving coefficient of approximately 4% for albumin, is also conceivable. Under dialysis conditions, that is to say a diffusion-controlled elimination of the substances intended for removal is primarily used, the albumin loss is less than 5-10 g per treatment. The EMiC$^2$ filter produced by the company Fresenius Medical Care can be cited as an example of a dialysis filter of this type. The flow conditions under which filters of this type are operated in clinical use are selected accordingly for a blood flow of 60-300 ml/min depending on use conditions: blood flows of 60-80 ml/min are used under the conditions of what is known as continuous veno-venous haemodialysis, whereas blood flows of 150-300 ml/min are used with dialysis device-assisted intermittent haemodialysis in acute cases, that is to say in patients with acute kidney failure, which also occurs very frequently in the case of sepsis. The dialysate flow in the case of intermittent haemodialysis is preferably set to 500 ml/min, whereas dialysate flows in a ratio of 1:1 to the blood flow are usual in the case of continuous veno-venous haemodialysis.

The concentration of the lipopeptide/polymyxin in the dialysis fluid should lie in the range of 0.2-1.0 μg/l, that is to say should be slightly higher than the controlled serum concentration value of the patient to be treated, since the sieving coefficient of the aforementioned dialysis filter is between 0.8 (AF 1000) and 0.9 (EMiC$^2$) that is to say between 80 and 90%.

The perfusion apparatus 700, for the automated control of the apparatus 700, is also assigned a controller 710, which is also connected to the pumps 703, 706, 709 via signal connections. The controller 710 is expediently also configured for central data acquisition and for data output.

1. EXAMPLE 1: Polymyxin B (PMB) Desorption in Plasma and Fractionated Plasma (Use of an Albuflow Filter) with Differently PMB-Coated Carrier (Mean Particle Size: 120 μm, Mean Pore Size: 15-20 nm)

1.1 PMB Coating

Carrier:

Amberchrom CG161c (polystyrene-divinylbenzene copolymer, Dow Chemical Company), mean particle size 120 am, mean pore size 15 nm; accessible surface 900 $m^2$/g polymer (dry). The dry weight per ml moist carrier is 18% (w/v).

Polymyxin B (PMB):

polymyxin B sulphate (Sigma Aldrich)

The PMB solution (10 mg/ml in dist. water) is autoclaved at 121° C., for 30 min, and the carrier is then coated in 15 ml Greiner tubes with PMB as follows (Table 1.1): 3 ml carrier with 7.5 ml PMB solution

TABLE 1.1

| PMB coating in mg per ml carrier | Carrier [ml] | PMB solution [ml] | NaCl [ml] |
|---|---|---|---|
| 0 | 3 | 0 | 7.5 |
| 1 | 3 | 0.3 | 7.2 |
| 2.5 | 3 | 0.75 | 6.75 |
| 5 | 3 | 1.5 | 6 |
| 7.5 | 3 | 2.25 | 5.25 |
| 10 | 3 | 3 | 4.5 |

The coating is carried overnight on a roll mixer at room temperature. The carrier is then washed twice with 10 ml NaCl solution (sterile), and a 50% suspension is produced.

1.2 Batch Test

Freshly frozen plasma (citrate plasma) was fractionated with the aid of the Albuflow® filter (Fresenius Medical Care, Germany) and was frozen at −20° C. together with the whole plasma.

A: whole plasma

B: fractionated plasma

TABLE 1.2

| | Batch approaches | | | | | |
|---|---|---|---|---|---|---|
| | 0 mg/ml | 1 mg/ml | 2.5 mg/ml | 5 mg/ml | 7.5 mg/ml | 10 mg/ml |
| A whole plasma | 0A 1 + 2 | 1A 1 + 2 | 2.5A 1 + 2 | 5A 1 + 2 | 7.5A 1 + 2 | 10A 1 + 2 |
| B fractionated plasma | 0B 1 + 2 | 1B 1 + 2 | 2.5B 1 + 2 | 5B 1 + 2 | 7.5B 1 + 2 | 10B 1 + 2 |

In the duplicate approach (see Table 1.2), every 0.5 ml of carrier are incubated with 4.5 ml of plasma=10% (v/v) approach at 37° C. for 60 min on an Enviro-genie. The carrier is then centrifuged off and the supernatant is used for PMB quantification by means of ELISA (polymyxin ELISA from Beijing Kwinbon Biotechnology Co., Ltd., China).

1.3 Results

Figure 8:
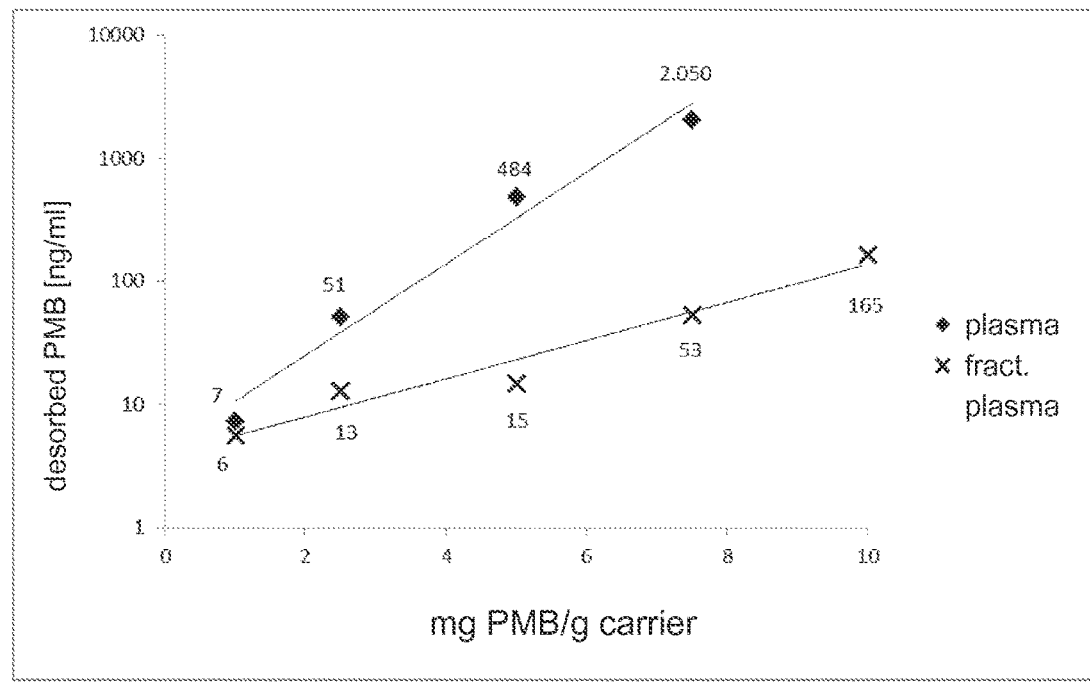
FIG. 8 shows a data plot showing the desorption of PMB in accordance with the PMB coating concentration.

With rising PMB concentration, the PMB solution used to coat the carrier desorbs a higher quantity of PMB in the plasma. The result is shown in FIG. 8 (desorption of PMB in accordance with the PMB coating concentration).

In order to achieve in the fractionated plasma a PMB plasma level of approximately 150 ng/ml by means of the desorption, the carrier used in this test has to be coated with 10 mg PMB per ml of adsorber.

2. EXAMPLE 2: Endotoxin Batch with Differently PMB-Coated Carrier in Serum

2.1 Test Structure

Conditioned carrier (Amberchrom CG161c: ethylvinylbenzene-divinylbenzene copolymer (Dow Chemical Company), mean particle size 120 m, mean pore size 15 nm) is coated with different quantity of polymyxin B (PMB): 0, 5, 10, 15 and 25 mg/g moist carrier. These are tested in a triplicate approach in an endotoxin batch test for LPS inactivation thereof in serum.

2.2 Test Execution

PMB Coating:

Carrier samples with different PMB concentrations (5 mg, 10 mg, 15 mg und 25 mg per g moist carrier) are produced (see protocol above in Example 1). The PMB solution (10 mg/ml in dist. water) and the carrier in 50% suspension are autoclaved at 121° C. for 30 min, and the carrier is coated in 15 ml Greiner tubes with PMB as follows (Table 2.2):

TABLE 2.2

| mg PMB/g adsorber | 50% adsorber suspension [ml] | PMB solution [ml] | NaCl [ml] |
|---|---|---|---|
| 0 | 2 | 0 | 3 |
| 5 | 2 | 0.5 | 2.5 |
| 10 | 2 | 1 | 2 |
| 15 | 2 | 1.5 | 1.5 |
| 25 | 2 | 2.5 | 0.5 |

The coating is performed for 4 hours on an overhead shaker (Enviro-Genie, frequency: 25:50) at room temperature. The carrier is then washed twice with 10 ml NaCl solution (sterile), and a 50% suspension is produced.

Production of Serum:

7 blood tubes (vacuette with serum beads for coagulation activation) measuring 8 ml are removed from the donor. The tubes filled with blood are left to stand for 30 min. The coagulated blood is then centrifuged and the serum obtained (cooled in a sterile Erlenmeyer flask).

Endotoxin (LPS) Solution:

LPS: *Pseudomonas aenruginosa*, L-7018 company Sigma batch: 128K4115, storage −70° C., at 100 µl $10^{-3}$ g/ml (1 mg/ml)

An LPS solution with a concentration of 10 µg/ml is produced from this LPS stock solution with sterile NaCl solution. The LPS is used in the batch with a final concentration of 5 ng/ml. 10 µl LPS solution with a concentration of 10 µg/ml are pipetted into 20 ml serum. The batch approach is performed in 2 ml blood-sampling tubes in a triplicate approach.

2.3 Results:

The LPS inactivation of more than 50% was able to be achieved already at the lowest coated PMB concentration.

Figure 9:
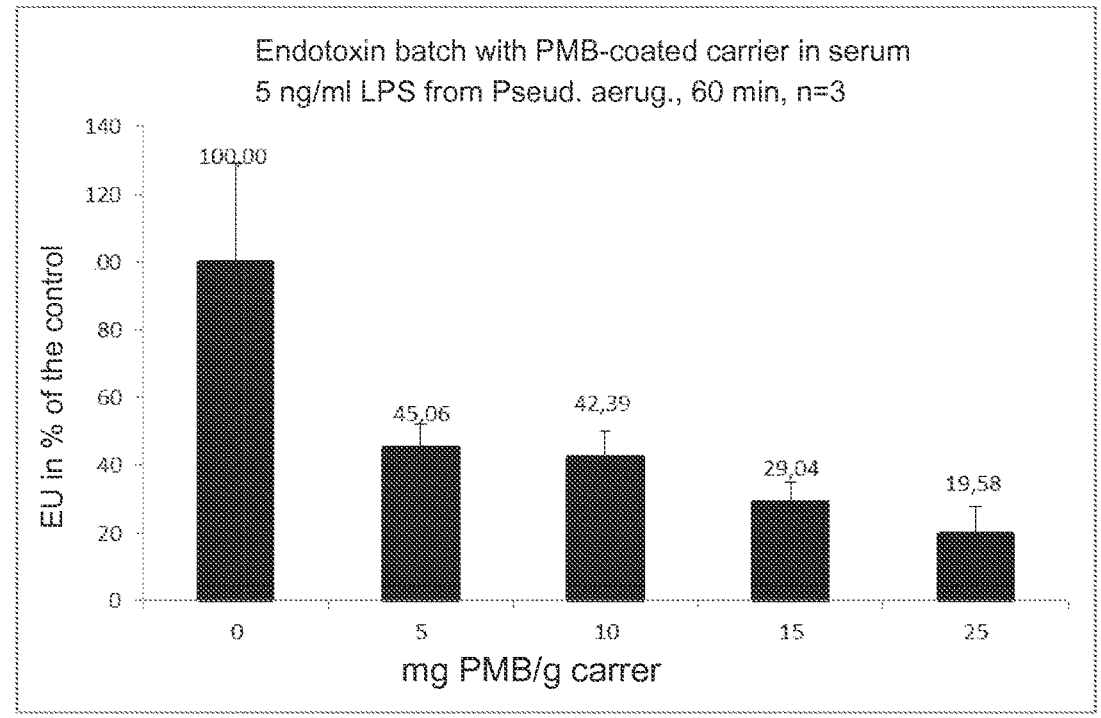
FIG. 9 shows a data plot shows ann LPS inactivation of more than 50% was able to be achieved at the lowest coarted PMB concentration (EU=endotoxin units).

The result is illustrated in FIG. 9 (EU=endotoxin units).

3. EXAMPLE 3: Endotoxin (LPS) Inactivation in Accordance with the Polymyxin-Concentration on the Basis of Endotoxins from *E. coli* and *Pseudomonas aeruginosa*

3.1. Objective

The objective of this test is to determine the polymyxin B (PMB) concentration-dependent endotoxin activation in plasma (batch test I). Furthermore, the extent to which this endotoxin activation results in an inhibition of cytokine distribution is to be examined (batch test II).

3.2. Blood Donor 9 blood-sampling tubes (each measuring 9 ml) spiked with 5 IU heparin are removed from a donor. The plasma is centrifuged off and the cell pellet incubated on a roll mixer. The plasma is spiked with endotoxin (LPS) and used for batch test I:

3.3. LPS Spike, Polymyxin B Solutions and Batch Test I

LPS: *Pseudomonas aeruginosa* (L-7018 company Sigma batch: 128K4115, −70° C., at 100 µl 10−3 g/ml (1 mg/ml))

LPS: *E. coli* (L-4130 company Sigma batch: 110M4086M, −70° C., at 100 µl 10−3 g/ml (1 mg/ml))

The LPS is used in the batch with a final concentration 0.5 ng/ml. The tests are carried out in 3 ml pyrogen-free glass vials. In batch test I, different PMB concentrations (company. Sigma, P-1004) are added in the duplicate approach and are incubated for 60 min on an overhead shaker at 37° C. (see Table 3.5).

In batch test 1, PMB concentrations with 0 (without PMB), 10, 100, 250, 500 and 1000 ng/ml are used. Sterile PMB solutions (autoclaved pyrogen-free at 121° C., 90 min) are produced for this purpose with the following concentrations (Table 3.3):

TABLE 3.3

| | PMB [ng/ml] | PMB [ng/ml] in Batch (1:15) |
|---|---|---|
| PMB solution A | 150 | 10 |
| PMB solution B | 1500 | 100 |
| PMB solution C | 3750 | 250 |
| PMB solution D | 7500 | 500 |
| PMB solution E | 15000 | 1000 |
| NaCl-solution | 0 | 0 |

The endotoxins are measured in the form of EU/ml with the aid of a Limulus Amebocyte Lysate test (LAL) by Charles River.

3.5. Cytokine Batch (Batch Test II)

The plasma spiked with LPS and PMB is fed back following batch test 1 to the cell concentrate obtained from the blood donor in the ratio 1:1 (see Table 3.5). For the cytokine batch, the samples from batch test I were used with a PMB concentration of 0 (without PMB), 250, 500 and 1000 ng/ml. As control, a sample without LPS and with 1000 ng/ml PMB was included. Following the incubation times of 4 h and 12 h at 37° C. on a roll mixer (5 revolutions/min), samples were taken, centrifuged off and 50 µl plasma were frozen at −80° C. for the subsequent cytokine quantification. The test data for the cytokine batch is listed in Table 3.5.

TABLE 3.5

| PMB [ng/ml] | PMB solution | Plasma + 0.5 ng/ml LPS | Incubation | LAL | EU/ml | Cytokine Batch | Sample 4 h | Sample 12 h |
|---|---|---|---|---|---|---|---|---|
| LPS *Pseudomonas aeruginosa* | | | | | | | | |
| 0 | 100 µl NaCl | 1400 µl | 60 min | #1 | 0.333 | 1500 µl cell concentrate + 1500 µl LPS-PMB plasma | 250 µl → 50 µl plasma −80° C. | 250 µl → 50 µl plasma −80° C. |
| 0 | 100 µl NaCl | 1400 µl | 60 min | #2 | 0.229 | | | |

TABLE 3.5-continued

| PMB [ng/ml] | PMB solution | Plasma + 0.5 ng/ml LPS | Incubation | LAL | EU/ml | Cytokine Batch | Sample 4 h | Sample 12 h |
|---|---|---|---|---|---|---|---|---|
| 10 | 100 µl sol A | 1400 µl | 60 min | #3 | 0.178 | | | |
| 10 | 100 µl sol A | 1400 µl | 60 min | #4 | 0.167 | | | |
| 100 | 100 µl sol B | 1400 µl | 60 min | #5 | 0.112 | | | |
| 100 | 100 µl sol B | 1400 µl | 60 min | #6 | 0.137 | | | |
| 250 | 100 µl sol C | 1400 µl | 60 min | #7 | 0.108 | 1500 µl cell concentrate + | 250 µl → | 250 µl → |
| 250 | 100 µl sol C | 1400 µl | 60 min | #8 | 0.123 | 1500 µl LPS-PMB plasma | 50 µl plasma −80° C. | 50 µl plasma −80° C. |
| 500 | 100 µl sol D | 1400 µl | 60 min | #9 | 0.091 | 1500 µl cell concentrate + | 250 µl → | 250 µl → |
| 500 | 100 µl sol D | 1400 µl | 60 min | #10 | 0.081 | 1500 µl LPS-PMB plasma | 50 µl plasma −80° C. | 50 µl plasma −80° C. |
| 1000 | 100 µl sol E | 1400 µl | 60 min | #11 | 0.062 | 1500 µl cell concentrate + | 250 µl → | 250 µl → |
| 1000 | 100 µl sol E | 1400 µl | 60 min | #12 | 0.061 | 1500 µl LPS-PMB plasma | 50 µl plasma −80° C. | 50 µl plasma −80° C. |
| LPS *E. coli* | | | | | | | | |
| 0 | 100 µl NaCl | 1400 µl | 60 min | #13 | 1.8 | 1500 µl cell concentrate + | 250 µl → | 250 µl → |
| 0 | 100 µl NaCl | 1400 µl | 60 min | #14 | 1.841 | 1500 µl LPS-PMB plasma | 50 µl plasma −80° C. | 50 µl plasma −80° C. |
| 10 | 100 µl sol A | 1400 µl | 60 min | #15 | 0.77 | | | |
| 10 | 100 µl sol A | 1400 µl | 60 min | #16 | 0.871 | | | |
| 100 | 100 µl sol B | 1400 µl | 60 min | #17 | 0.379 | | | |
| 100 | 100 µl sol B | 1400 µl | 60 min | #18 | 0.382 | | | |
| 250 | 100 µl sol C | 1400 µl | 60 min | #19 | 0.281 | 1500 µl cell concentrate + | 250 µl → | 250 µl → |
| 250 | 100 µl sol C | 1400 µl | 60 min | #20 | 0.29 | 1500 µl LPS-PMB plasma | 50 µl plasma −80° C. | 50 µl plasma −80° C. |
| 500 | 100 µl sol D | 1400 µl | 60 min | #21 | 0.209 | 1500 µl cell concentrate + | 250 µl → | 250 µl → |
| 500 | 100 µl sol D | 1400 µl | 60 min | #22 | 0.209 | 1500 µl LPS-PMB plasma | 50 µl plasma −80° C. | 50 µl plasma −80° C. |
| 1000 | 100 µl sol E | 1400 µl | 60 min | #23 | 0.154 | 1500 µl cell concentrate + | 250 µl → | 250 µl → |
| 1000 | 100 µl sol E | 1400 µl | 60 min | #24 | 0.16 | 1500 µl LPS-PMB plasma | 50 µl plasma −80° C. | 50 µl plasma −80° C. |

3.6. Results

Figure 10:
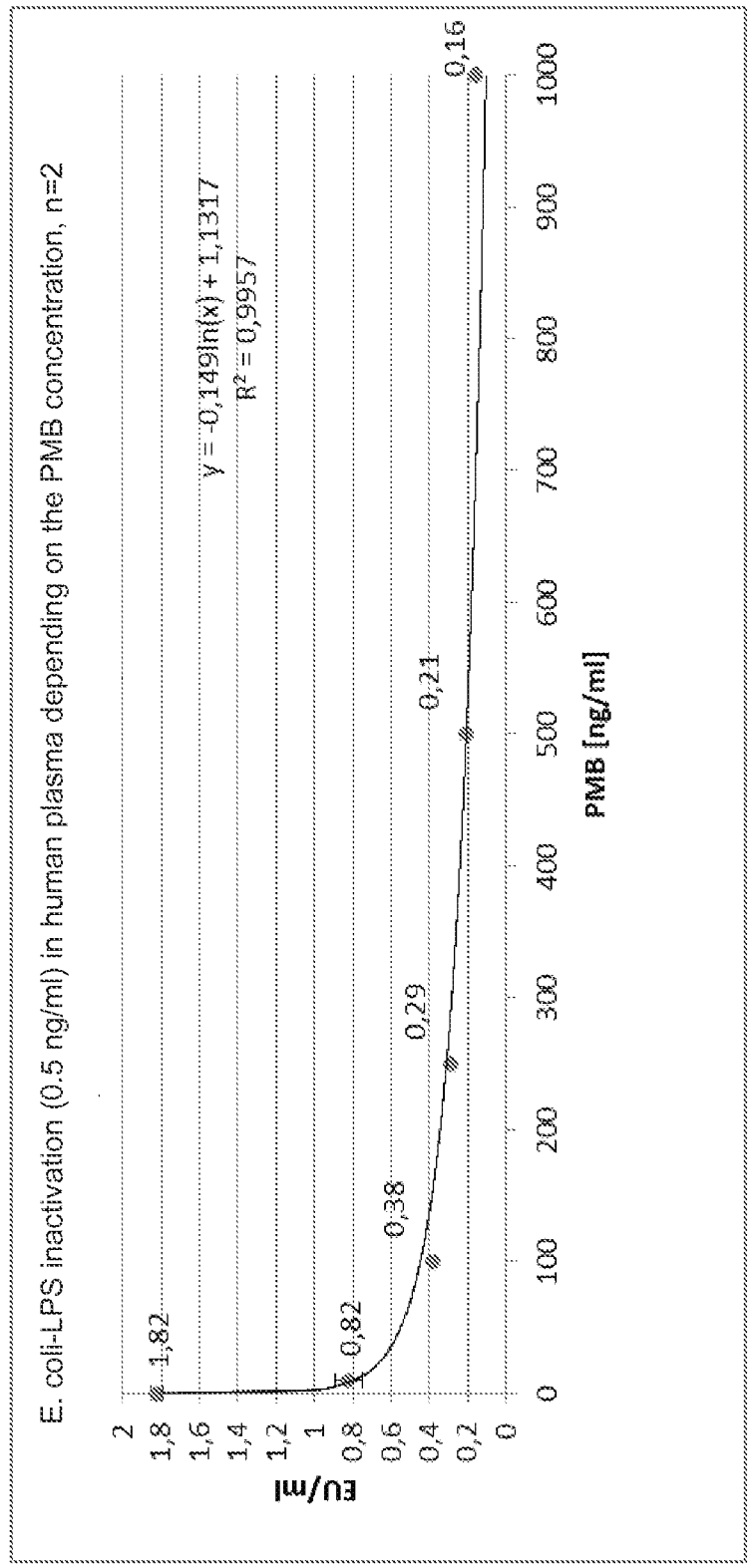
FIG. 10 shows the inhibition of LPS from *E. coli* in plasma (original LPS concentration: 0.5 ng/ml) in accordance with the PMB concentration (n=2) following an incubation time of 60 min.

Endoloxin Batch (Batch Test I):

FIG. 10 shows the inhibition of LPS from *E. coli* in plasma (original LPS concentration: 0.5 ng/ml) in accordance with the PMB concentration (n=2) following an incubation time of 60 min.

Figure 11:
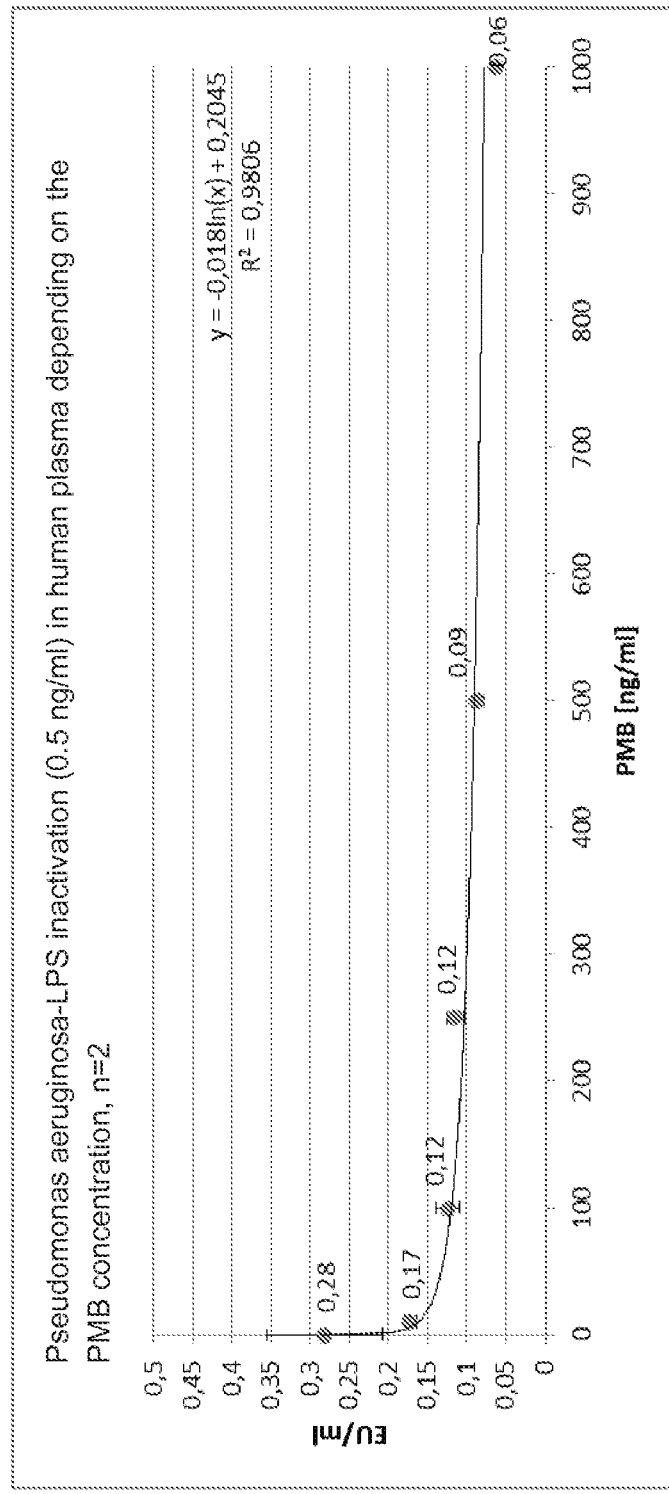
FIG. 11 shows the inhibition of LPS from *Pseudomonas aeruginosa* in plasma (original LPS concentration: 0.5 ng/ml) in accordance with the PMB concentration (n=2) following an incubation time of 60 min.

FIG. 11 shows the inhibition of LPS from *Pseudoonas aeruginosa* in plasma (original LPS concentration: 0.5 ng/ml) in accordance with the PMB concentration (n=2) following an incubation time of 60 min.

The results clearly show that, even with a very low PMB concentration in the plasma, that is to say in a range from 50 to 300 ng/ml (0.05 to 0.3 µg/ml), a strong inhibition of LPS from *E. coli* and *Pseudomonas aeruginosa* takes place, wherein the LPS inhibition no longer increases significantly with rising PMB concentration. As a result, even very low concentrations of PMB are sufficient in order to inhibit the activity of LPS (endotoxins). Neurotoxic and nephrotoxic side effects are to be ruled out at these low concentrations.

Figure 12:
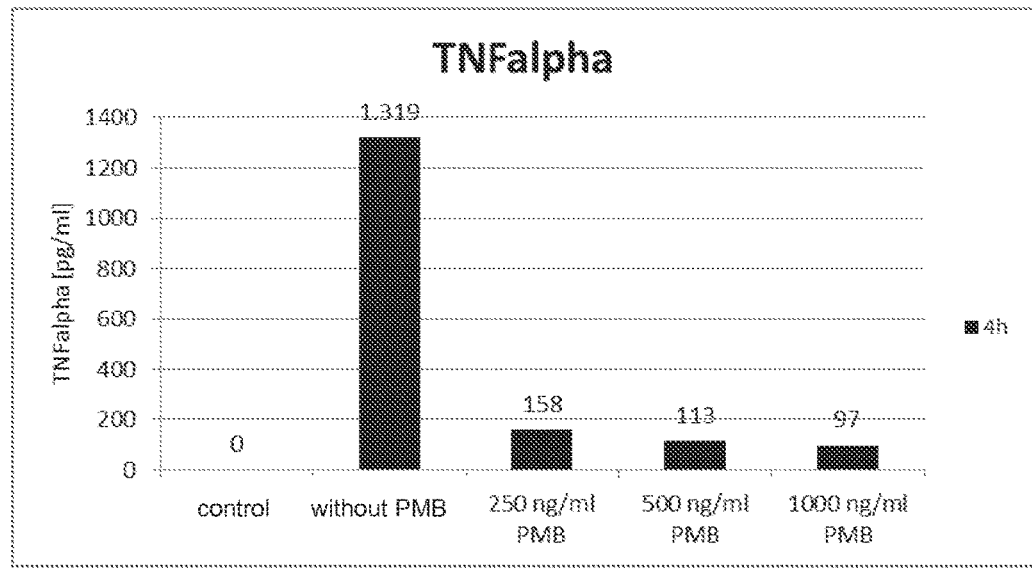
FIG. 12 shows the distrobution of TNF-alpha cytokines by the blood cells in accordance with the PMB concentration (without PMB, 250 ng/ml, 500 ng/ml and 1000 ng/ml; control with 1,000 ng/ml without LPS).
Figure 13:
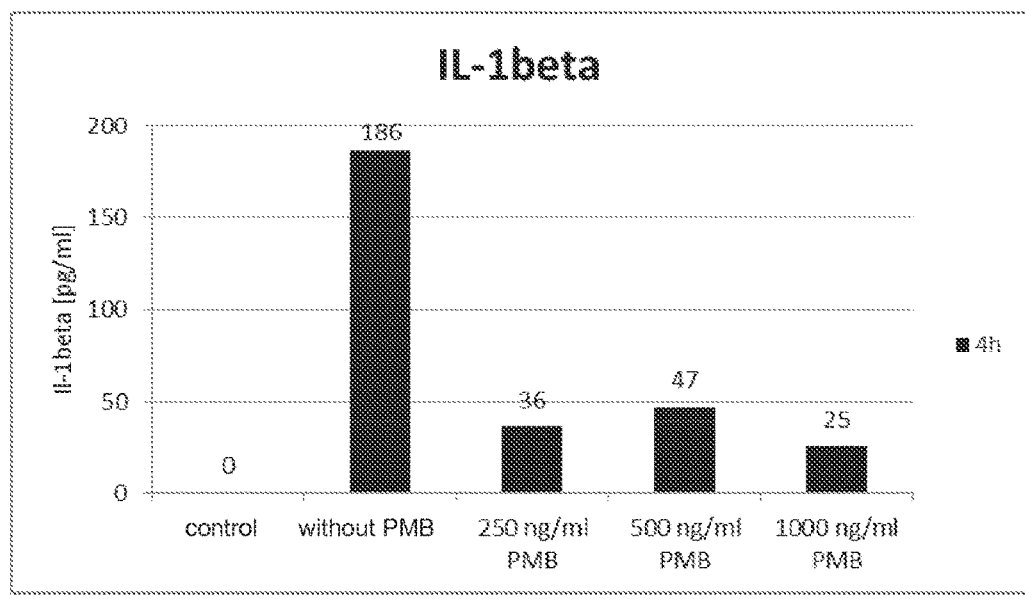
FIG. 13 shows the distribution of IL-1beta cytokines by the blood cells in accordance with the PMB concentration (without PMB, 250 ng/ml, 500 ng/ml and 1000 ng/ml; control with 1,000 ng/ml without LPS).
Figure 14:
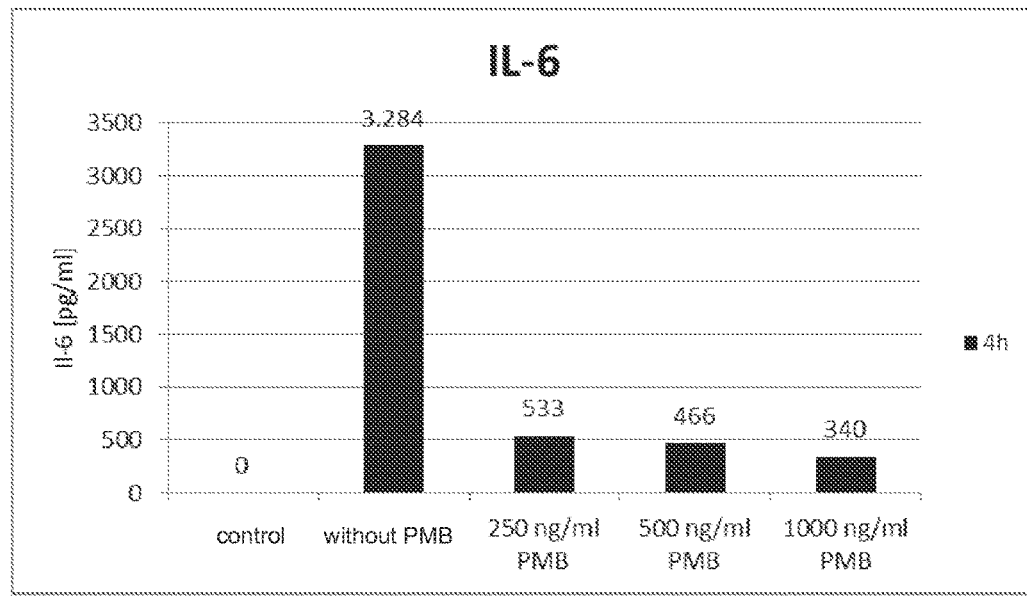
FIG. 14 shows the distribution of IL-6 cytokines by the blood cells in accordance with the PMB concentration (without PMB, 250 ng/ml, 500 ng/ml and 1000 ng/ml; control with 1,000 ng/ml without LPS).
Figure 15:
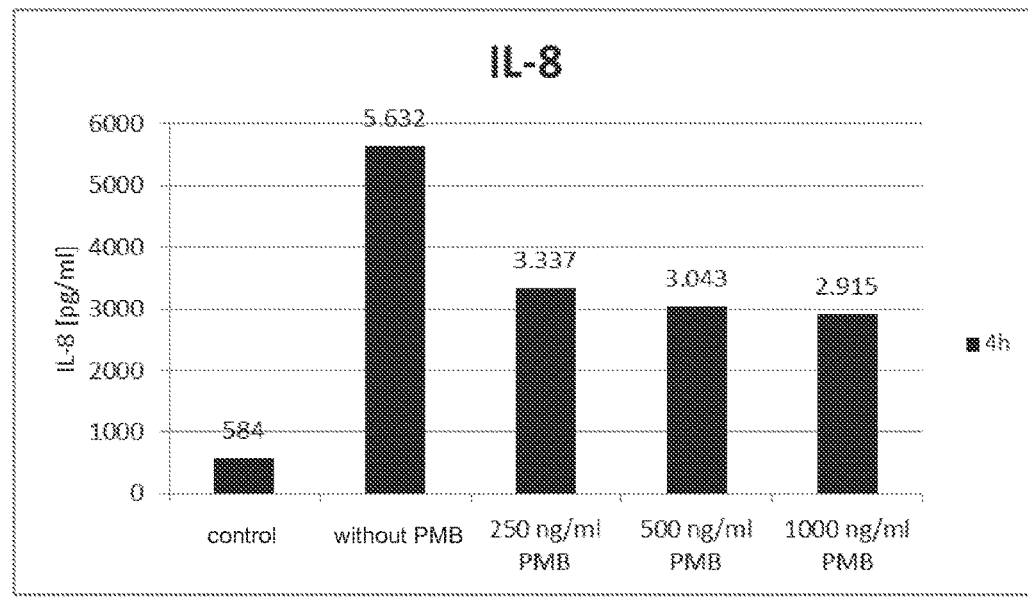
FIG. 15 shows the distribution of IL-8 cytokines by the blood cells in accordance with the PMB concentration (without PMB, 250 ng/ml, 500 ng/ml and 1000 ng/ml; control with 1,000 ng/ml without LPS).

Cytokine Batch (Batch Test II):

The distribution of the cytokines TNF-alpha (FIG. 12), IL-1beta (FIG. 13), IL-6 (FIG. 14) and IL-8 (FIG. 15) by the blood cells in accordance with the PMB concentration (without PMB, 250 ng/ml, 500 ng/ml and 1000 ng/ml; control with 1,000 ng/ml without LPS) in LPS (*E. coli*)-spiked plasma after 4 hours incubation is illustrated in FIGS. 3 to 4. The results from batch test II clearly show that, even at very low PMB concentrations, not only a strong inhibition of LPS (see batch test I), but subsequently also a strong inhibition of the cytokine distribution takes place. This is particularly pronounced in the case of the inhibition of the key mediator TNF-alpha (FIG. 12).

4. EXAMPLE 4: Examples for Formulations for Preparations for Parenteral Administration of Polymyxin B (PMB)-Injection Solutions (for Bolus Administration)

4.1. Bolus Administration for a PMB Serum Concentration of 100 ng/ml Plasma

Assumption: patient with 70 kg body weight and 60% of the body weight are distribution volumes for PMB→42000 ml distribution volumes.

A PMB serum concentration of 100 ng PMB/ml plasma is sought→a total of 4.2 mg PMB are required.

Injection solution for bolus administration over a period of 60 min: 4.2 mg PMB in 100 ml physiological saline solution=finished injection solution for bolus administration over a period of 60 min.

4.2. Bolus Administration for a PMB Serum Concentration of 250 ng/ml Plasma

Assumption: patient with 70 kg body weight and 60% of the body weight are distribution volumes for PMB→42000 ml distribution volumes.

A PMB serum concentration of 250 ng PMB/ml plasma is sought→a total of 10.5 mg PMB are required.

Injection solution for bolus administration over a period of 120 min: 10.5 mg PMB in 100 ml physiological saline solution=finished injection solution for bolus administration over a period of 120 min.

As soon as the desired PMB serum concentration is set by the bolus administration, this is maintained by PMB release by means of the dispensing means associated with the perfusion apparatus according to several embodiments of the invention, as described above.

5. EXAMPLE 5: Examples for Infusion Solutions for Infusion of Polymyxin B (Pmb) in the Extracorporeal Blood Circuit at a Lipid Feed Point and Also Dosing Instructions Assumption: patient with 70 kg→distribution volume for PMB (60% of the body mass) 42000 ml body fluid with 100 ng PMB/ml→4.2 mg PMB in the distribution volume (see under 2.1.1.).

Infusion solution for a 24 h infusion with a serum half-life of 6 h: assumed half-life for PMB in serum 6 h: 2.1 mg PMB per 6 h or 8.4 mg PMB/day are broken down→8.4 mg PMB in 1 L physiological saline solution=infusion solution for 24 h infusion.

Infusion solution for a 24 h infusion with a serum half-life of 14 h: half-life for PMB in serum 14 hours: 4.2 mg PMB/14 h or 7.2 mg PMB/day are broken down→7.2 mg PMB in 1 L physiological saline solution=infusion solution for 24 h infusion.

6. EXAMPLE 6: Dosing Instructions for Infusion of Polymyxin B (PMB) in the Extracorporeal Blood Circuit at a Lipid Feed Point Under Consideration of the PMB Total Clearance of the Perfusion Apparatus The following calculation example, besides the PMB patient clearance, also takes into consideration the clearance of a dialyser (dialysis filter) arranged in the extracorporeal blood circuit and the clearance of the carrier of the depletion agent. The calculation example presupposes an existing PMB serum concentration. This is provided by administration of a bolus prior to the start of the treatment, wherein the injection solutions described under Example 4 can be used for this purpose.

For the calculation of the dosing of polymyxin B via infusion in the extracorporeal blood circuit at a lipid feed point, the PMB clearance of the patient body, of the dialyser and of the depletion agent are taken into consideration:

- The PMB dialysis clearance (CDial) can be determined experimentally and is dependent on the plasma flow and also on the dialysis filter type used. In the specified example, this is 60 ml/min.
- The PMB clearance of the depletion agent (Cads) is dependent on the carrier material used and also on the filtrate flow. In the specified example, this is 45 ml/min.
- The PMB patient clearance was determined in the specified example from the half-life for PMB of 13.6 and is 36 ml/min.

Figure 16:
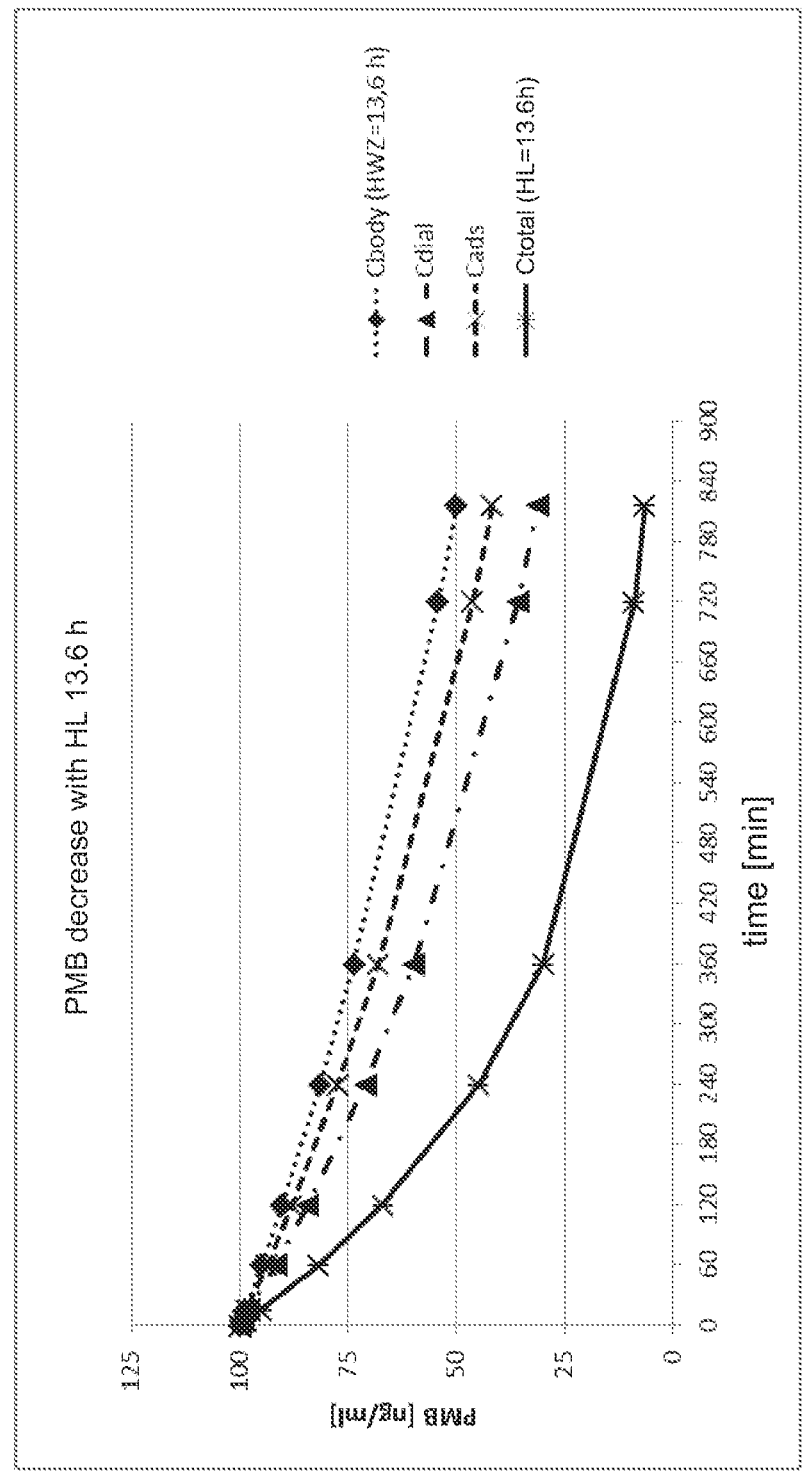
FIG. 16 shows the PMB total clearance (Ctotal) given by addition from the individual PMB clearance rates.

The PMB total clearance (Ctotal) is given by addition from the individual PMB clearance rates. The resultant decrease of PMB is illustrated in FIG. 16. The evident negative rise of the PMB decrease (Ctotal) at a certain moment in time clear in FIG. 16 corresponds to the necessary PMB infusion in order to maintain the PMB serum concentration of the associated moment in time.

The following infusion rates are given for the specified example:
=>0.84 mg PMB/h during the treatment with dialysis and adsorption With 6-hour extracorporeal treatment, this gives the following PMB quantity to be infused:
6 hours treatment with dialysis and adsorption: 5.1 mg

7. EXAMPLE 7: Improved Adsorption of Cytokines by the Use of an Albuflow Filter (Comparison of Plasma and Fractionated Plasma)

7.1 Batch Test Cytokine Adsorption
Test Description:
Adsorbers with different pore sizes (30 nm and 15-20 nm) are to be tested in terms of adsorption of TNFa, IL-6 and IL-10 in whole plasma and in fractionated plasma.
Test Structure:
Carrier: polystyrene-divinylbenzene copolymer, CG300c (carrier A), CG161c (carrier B), Dow Chemical Group carrier A: particle size: 120 μm, pore size: 30 nm
carrier B: particle size: 120 μm, pore size: 15-20 nm
plasma: deep-frozen unfractionated citrate plasma (fresh frozen plasma, obtained by means of blood centrifugation)
fractionated citrate plasma: obtained by the use of the Albuflow-Filters (Fresenius Medical Care, Germany).
Cytokine spike (TNF-α, IL-6, IL-10) according to Table 7.1 below.

Carriers A and B are conditioned: the carrier is washed with 2.5 volume of ethanol absolute and the carrier is centrifuged off. The supernatant is rejected and the carrier is incubated for 1 hour at room temperature with 2.5 times volume ethanol absolute, then centrifuged off, and the supernatant is rejected once again. The same procedure is then carried out with twice-distilled water and lastly with physiological saline solution. Following the conditioning, the carrier is additionally washed again 3× with 0.9% NaCl solution The batch test is carried out in triplicate approach both in whole plasma and in fractionated plasma (pre-treatment by the Albuflow filter).

Before the test is started, the carriers are incubated with unspiked whole plasma or with fractionated plasma for 15 min, washed, 1× with NaCl and then used for the batch test.

Batch test: In each case 1 ml adsorber (moist)+9 ml citrate plasma on a roll mixer at 37° C. for 60 min.

TABLE 7.1

| | Batch number | Stock concentration [μg/ml] | Stock dilution 1:10 | Stock dilution to 40 ml Plasma | Expected end concentration in the plasma [pg/ml] | Measured and concentration in the plasma |
|---|---|---|---|---|---|---|
| TNF-α | AA27/1082 | 10 | 10 stock + 90NaCl | 8 μl | 500 | 625 |
| IL-6 | OJZ0411121 | 10 | 10 stock + 90NaCl | 35 μl | 200 | 355 |
| IL-10 | EYB0211041 | 10 | 10 stock + 90NaCl | 80 μl | 300 | 517 |

Figure 17:
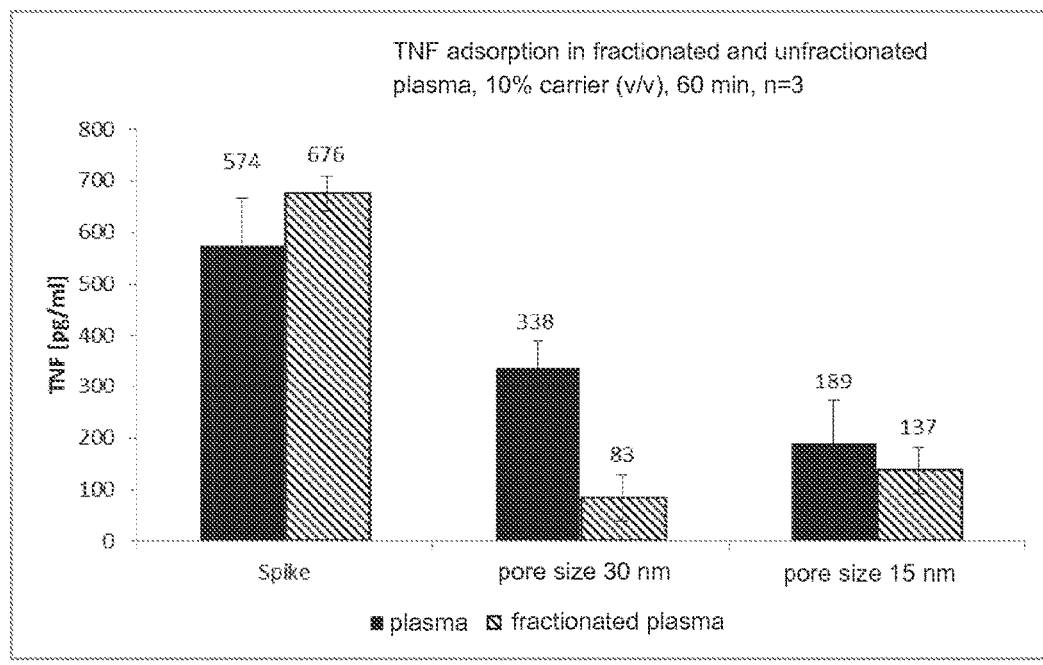
FIG. 17 shows the improved adsorption of TNF-α cytokines by use of an Albuflow filter compared with a plasma filter.
Figure 18:
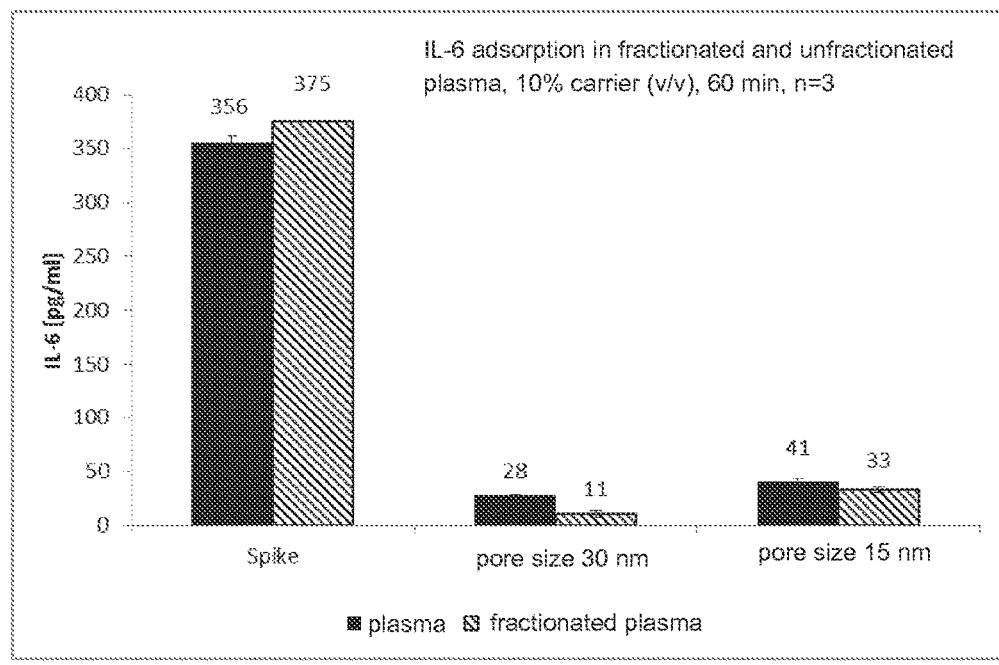
FIG. 18 shows the improved adsorption of IL-6 cytokines by use of an Albuflow filter compared with a plasma filter.
Figure 19:
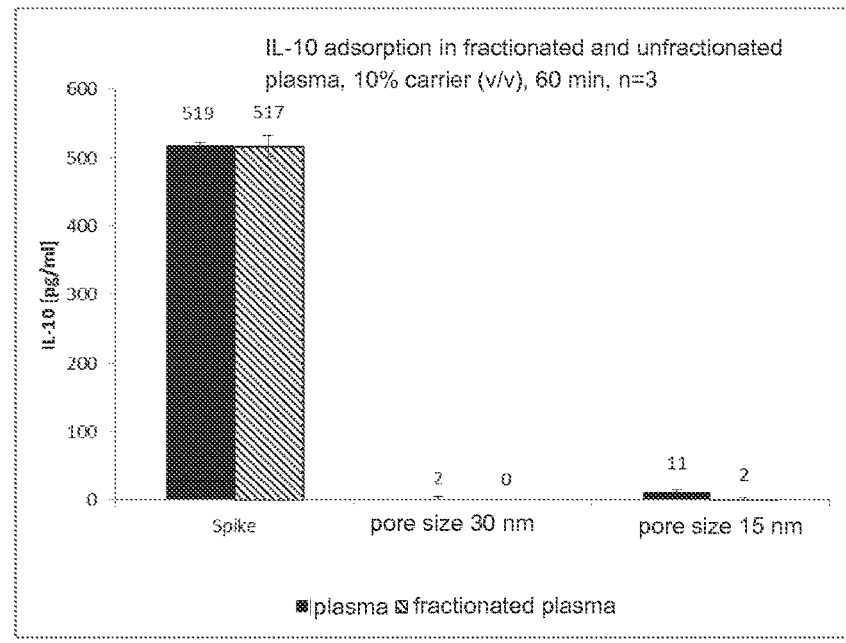
FIG. 19 shows the improved adsorption of IL-10 cytokines by use of an Albuflow filter compared with a plasma filter.

Analyses:
TNFa, IL-6 and IL-10 were quantified by means of commercial ELISA from the company R&D Systems.
7.2 Results
It was possible to determine improved cytokine adsorption in the fractionated plasma.
FIG. 17-19 show the improved adsorption of the cytokines TNF-α, IL-6 and IL-10 by use of an Albuflow filter compared with a plasma filter.

8. EXAMPLE 8: Testing of Ethylvinylbenzene-Divinylbenzene Copolymers of Identical Pore Size and Different Particle Size in Terms of the Adsorption Properties Thereof Ethylene vinylbenzene-divinylbenzene copolymers (carrier) with identical mean pore sizes (15-20 nm), but with different mean particle sizes of 3-5 μm, 35 μm, 75 μm and 120 μm are compared in terms of the adsorption property for protein C.
8.1 Provision of Neutral, Hydrophobic Polymers
The ethylene vinylbenzene-divinylbenzene copolymers used in this example (Amberchrom CG 161, Rohm&Haas/Dow Chemical Company) with identical mean pore size and different mean particle size are listed in Table 8.1.

TABLE 8.1

Ethylvinylbenzene-divinylbenzene copolymers

| Naming of the ethylvinylbenzene-divinylbenzene copolymer | Mean pore size [nm] | Mean particle size [μm] |
|---|---|---|
| #2000 | 15-20 | 3-5 |
| #1785 | 15-20 | 35 |
| #1760 | 15-20 | 75 |
| #2004 | 15-20 | 120 |

8.2. Carrier Preparation and Batch Test

The carriers #2000, #1785, #1760 and #2004 specified in Table 8.1 were tested in the batch test in terms of the adsorption properties thereof for protein C and were compared with one another.

The carriers were conditioned and incubated for 15 min in plasma directly prior to the batch test, centrifuged off and then used in the batch test.

Conditioning of carriers: dry carriers should be conditioned prior to use in order to enable good wetting with aqueous solutions or with plasma. Dry, hydrophobic carriers are pretreated as follows: the required quantity of dry carrier is placed in a 50 ml Greiner tube and washed with 5 times volume of undenatured ethanol (suspended and centrifuged for 5 min at 4000 rpm). The supernatant is removed and discarded and suspended again with fresh, undenatured ethanol and incubated for 1 h (Enviro Genie, frequency 25:50). Following incubation, the carrier suspension is centrifuged off (centrifuged for 5 min at 4000 rpm) and the supernatant is discarded. The carrier is then washed with 5 times volume of distilled water (suspended and centrifuged for 5 min at 4000 rpm). The supernatant is removed and discarded and suspended again with fresh distilled water and incubated for 1 h (Enviro Genie, frequency 25:50). Following incubation the carrier suspension is centrifuged off (centrifuged for 5 min at 4000 rpm) and the supernatant is discarded. The carrier is then washed with 5 times volume of physiological saline solution (suspended and centrifuged for 5 min at 4000 rpm). The supernatant is removed and discarded and suspended again with fresh physiological saline solution and is incubated for 1 h (Enviro Genie, frequency 25:50). Following incubation, the carrier suspension is centrifuged off (centrifuged for 5 min at 4000 rpm) and the supernatant is discarded. A 50% carrier suspension is ultimately produced with physiological saline solution and is stored in a refrigerator until use.

For the batch approach (triplicate approach, n=3) 150 μl carriers (moist) were each coated with 1350 μl citrate plasma in 15 ml Greiner tubes. The tubes were shaken in the Enviro-Genie at 25/50 rpm at 37° C. for 60 min. As control (120 μl NaCl+1350 μl citrate plasma), a tube without carrier was included.

Samples each measuring 500 μl were taken after 15 min and after 60 min for the Protein C analysis. Protein C was analysed on the Sysmex (Siemens, CA560) with the associated reagents (Siemens, OUVV17).

8.3. Analyses and Results

Figure 20:
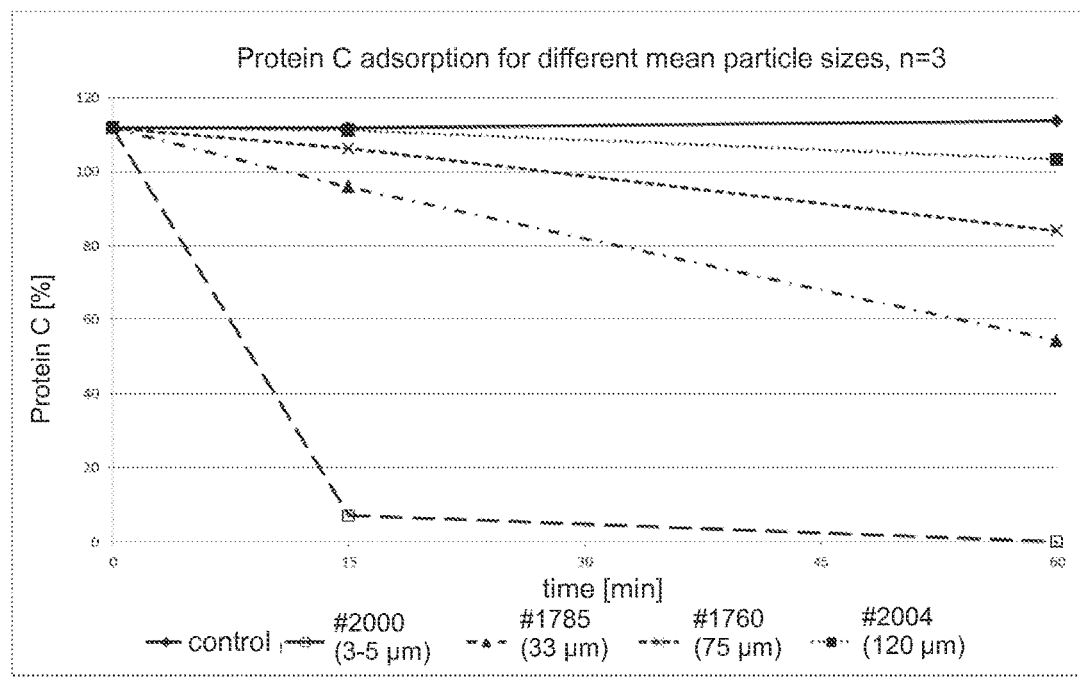
FIG. 20 shows the protein C concentration (specification in [%] in relation to the physiological protein C concentration in human plasma) over time for the individual carriers.
Figure 21:
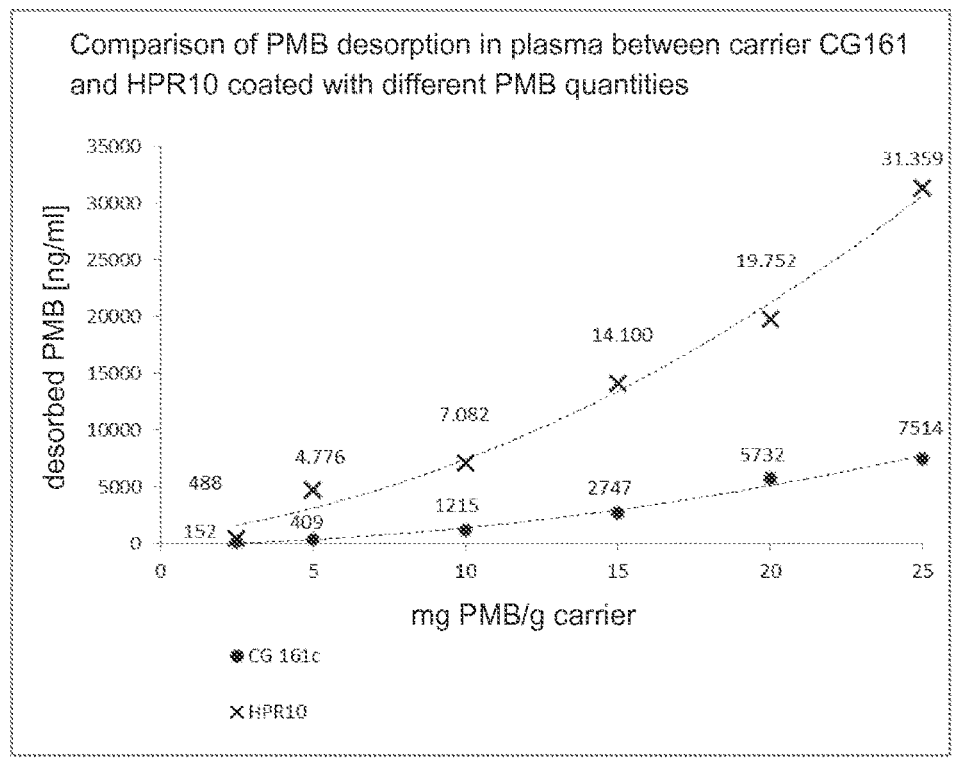
FIGS. 21 to 24 show the desorption rate of polymyxin in plasma across various available carrier surfaces.
Figure 22:
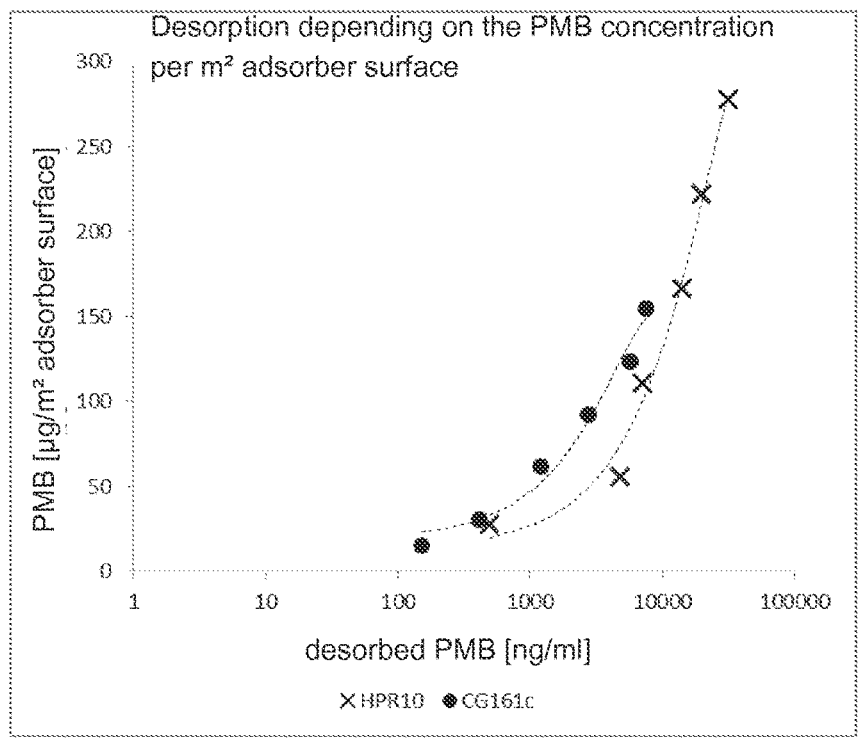
Figure 23:
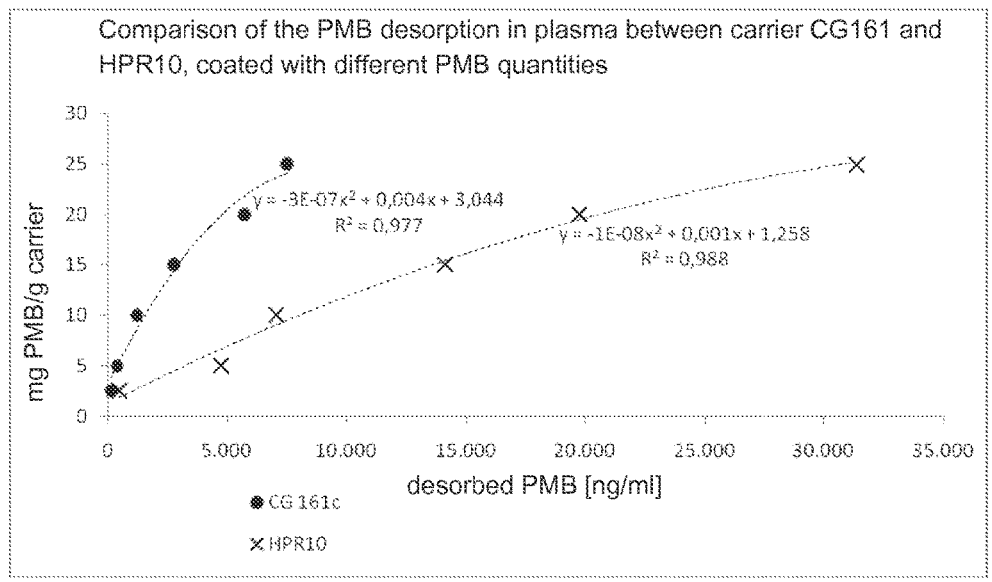
Figure 24:
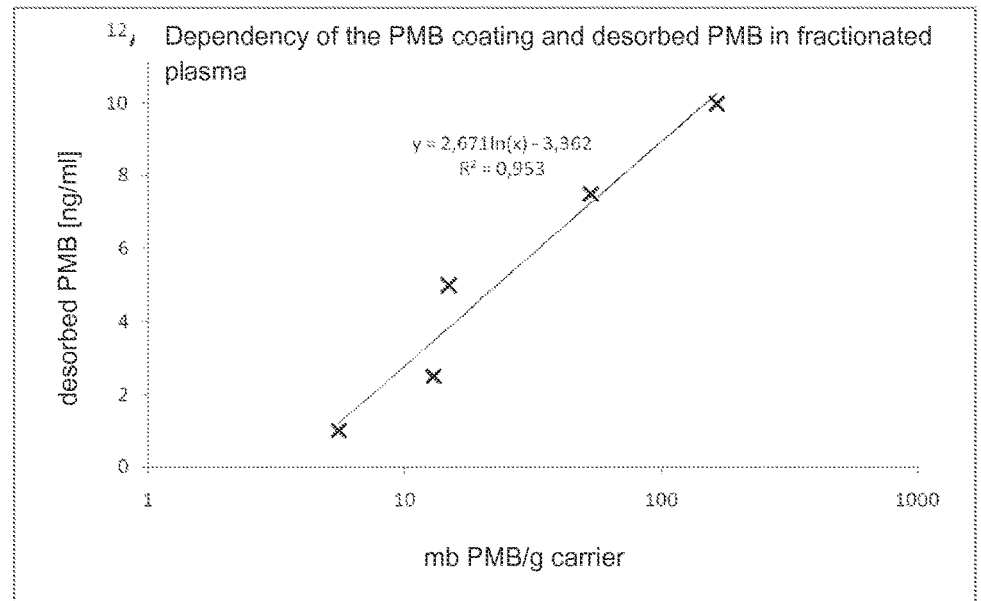

FIG. 20 shows the protein C concentration (specification in [%] in relation to the physiological protein C concentration in human plasma) over time for the individual carriers. On the basis of the curves, the dependency of the protein C adsorption on the mean particle size is clearly evident. A pronounced protein C adsorption was determined with carriers #2000 and #1785. In the case of carrier #2000, protein C was removed almost completely from the plasma after just 15 minutes. By contrast, protein C was adsorbed from the plasma to a much smaller extent by carriers #1760 and #2004. The protein C reduction of 25% observed for carrier #1760 (after 60 min incubation) is still in a range in which physiologically relevant quantities of protein C remain in the plasma. The lowest protein C adsorption, which was just 8% in relation to the protein C starting concentration after 60 min incubation, was determined for carrier #2004. The protein C adsorption (in % in relation to the protein C starting concentration) by the individual carriers is listed in Table 8.3.

TABLE 8.3

| Carrier: | Protein C adsorption after 15 min incubation | Protein C adsorption after 60 min incubation |
|---|---|---|
| #2000 | 94% | 99% |
| #1785 | 14% | 52% |
| #1760 | 5% | 25% |
| #2004 | 1% | 8% |

9. EXAMPLE 9: Comparison of the PMB Desorption in Plasma Between Adsorbers with Different Pores and Particle Size and Thus Different Available Adsorption Surface 9.1 Carriers CG161c:

The carrier (Rohm & Haas/Dow Chemical Company; also referred to hereinafter as adsorber) consists of a porous polystyrene-divinylbenzene matrix. The average pore size is 15 nm, the average particle size is 120 μm and the accessible surface is 900 m²/g adsorber (dry). The dry weight per ml of moist adsorber is 18% (w/v).

HPR10:

The carrier (Rohm & Haas/Dow Chemical Company; also referred to hereinafter as adsorber) consists of a porous polystyrene-divinylbenzene matrix. The average pore size is 30-40 nm, the average particle size is 10 μm and the accessible surface is 500 m²/g adsorber (dry). The dry weight per ml of moist carrier is 30% (w/v).

9.2 Coating of the Carrier with Polymyxin B (PMB)

The PMB solution (Sigma Aldrich, 10 mg/ml in dist. water) is autoclaved at 121° C. for 30 min, and the respective carrier (CG161c or HPR10) is then coated in 15 ml Greiner tubes with PMB as follows (Table 92): 3 ml carrier with 7.5 ml PMB solution

TABLE 9.2

| PMB coating in mg per ml carrier | Carrier [ml] | PMB solution [ml] | NaCl [ml] |
|---|---|---|---|
| 0 | 3 | 0 | 7.5 |
| 2.5 | 3 | 0.75 | 6.75 |
| 5 | 3 | 1.5 | 6 |
| 10 | 3 | 3 | 4.5 |
| 15 | 3 | 4.5 | 3 |
| 20 | 3 | 1.5 | 6 |
| 25 | 3 | 0 | 7.5 |

The coating is performed overnight on a roll mixer at room temperature. The adsorber is then washed twice with 10 ml NaCl solution (sterile), and a 50% suspension is produced.

9.3 Batch Test

In the duplicate approach, 0.5 ml carrier suspension is incubated in each case with 4.5 ml citrate plasma=10% (v/v) at 37° C. for 60 min in an Enviro-genie. The carrier is then centrifuged off and the supernatant is used for the PMB quantification by means of ELISA (polymyxin-ELISA from Beijing Kwinbon Biotechnology Co., Ltd., China).

9.4 Result

It is clear from the result (see FIG. 21, FIG. 22, FIG. 23 and FIG. 24) that the desorption rate of polymyxin in plasma is very heavily dependent on the available carrier surface. This means that the desorption of polymyxin is dependent on the quantity of hydrophobically bonded polymyxin per $m^2$. This is also clear from the following calculation tables (Table 9.4.1 and Table 9.4.2).

TABLE 9.4.1

Example CG161c

| mg PMB/ml adsorber | PMB desorption [ng/ml] | Surface [$m^2$/g adsorber (dry)] | Dry component % [w/v] | Surface [$m^2$/ml adsorber (moist)] | PMB [$\mu g/m^2$ adsorber surface] |
| --- | --- | --- | --- | --- | --- |
| 2.5 | 152 | 900 | 18 | 162 | 15 |
| 5 | 409 | 900 | 18 | 162 | 31 |
| 10 | 1215 | 900 | 18 | 162 | 62 |
| 15 | 2747 | 900 | 18 | 162 | 93 |
| 20 | 5732 | 900 | 18 | 162 | 123 |
| 25 | 7514 | 900 | 18 | 162 | 154 |

TABLE 9.4.2

Example HPR10

| mg PMB/ml adsorber | PMB desorption [ng/ml] | Surface [$m^2$/g adsorber (dry)] | Dry component % [w/v] | Surface [$m^2$/ml adsorber (moist)] | PMB [$\mu g/m^2$ adsorber surface] |
| --- | --- | --- | --- | --- | --- |
| 2.5 | 488 | 300 | 30 | 90 | 28 |
| 5 | 4776 | 300 | 30 | 90 | 56 |
| 10 | 7082 | 300 | 30 | 90 | 111 |
| 15 | 14100 | 300 | 30 | 90 | 167 |
| 20 | 19752 | 300 | 30 | 90 | 222 |
| 25 | 31359 | 300 | 30 | 90 | 278 |

9.5 Calculation Examples

In order to precisely define the PMB concentration in the plasma during a treatment by the PMB desorption from the carrier (also referred to hereinafter as adsorber), in vitro desorption experiments (as carried out in Example 9) are necessary for the respective adsorber. It is possible to very accurately adjust the desorption in the plasma and therefore the PMB concentration in the plasma by the degree of coating of the carrier (quantity of PMB per g adsorber) on the basis of the data obtained in the experiments (See FIG. 21 to 24). As shown in Example 1, the desorption rate in the fractionated plasma could be lower and could therefore be determined separately.

CALCULATION EXAMPLE 1

A PMB concentration in the plasma of 0.8 µg/ml is to be obtained by the use of the PMB-coated adsorber HPR10 in the extracorporeal blood circuit. Due to preliminary tests (See FIG. 23), the function describing the correlation between coated PMB quantity per g adsorber and desorbed PMB quantity in the plasma was able to be determined by way of experiment. In this case, it is as follows:

$$PMB\left[\frac{mg}{g\ adsorber}\right] = 0.00000001x^2 + 0.0012x + 1.258$$

x=desired PMB concentration in plasma=0.8 µg/ml=800 ng/ml

If x=800 ng/ml is used, the PMB quantity that has to be bonded hydrophobically per g carrier is: 2.224 mg per g carrier (HPR10)

CALCULATION EXAMPLE 2

A PMB concentration in the plasma of 0.8 µg/ml is to be obtained by the use of the PMB-coated adsorber CG161c in the extracorporeal blood circuit. Due to preliminary tests (See FIG. 23), the function describing the correlation between coated PMB quantity per g adsorber and desorbed PMB quantity in the plasma was able to be determined by way of experiment. In this case, it is as follows:

$$PMB\left[\frac{mg}{g\ adsorber}\right] = 0.00000003x^2 + 0.0048x + 3.0442$$

x=desired PMB concentration in plasma=0.8 µg/ml=800 ng/ml

If x=800 ng/ml used, the PMB quantity that must be bonded hydrophobically per g adsorber is: 7.076 mg pro g adsorber (CG161c)

CALCULATION EXAMPLE 3

A PMB concentration in the plasma of 0.1 µg/ml is to be obtained by the use of the PMB-coated adsorber HPR10 in the extracorporeal blood circuit. Due to preliminary tests (See FIG. 23), the function describing the correlation between coated PMB quantity per g adsorber and desorbed PMB quantity in the plasma was able to be determined by way of experiment. In this case, it is as follows:

$$PMB\left[\frac{mg}{g\ adsorber}\right] = 0.00000001x^2 + 0.0012x + 1.258$$

x=desired PMB concentration in plasma=0.1 µg/ml=100 ng/ml if x=100 ng/ml used, the PMB quantity that must be bonded hydrophobically per g adsorber is: 1.378 mg pro g adsorber (HPR10)

CALCULATION EXAMPLE 4

A PMB concentration in the plasma of 0.1 µg/ml is to be obtained by the use of the PMB-coated adsorber CG161c in the extracorporeal blood circuit. Due to preliminary tests (See FIG. 23), the function describing the correlation between coated PMB quantity per g adsorber and desorbed PMB quantity in the plasma was able to be determined by way of experiment. In this case, it is as follows:

$$PMB\left[\frac{mg}{g\ adsorber}\right] = 0.00000003x^2 + 0.0048x + 3.0442$$

x=desired PMB concentration in plasma=0.1 µg/ml=100 ng/ml

If x=100 ng/ml used, the PMB quantity that must be bonded hydrophobically per g adsorber is: 3.527 mg pro g adsorber (CG161c)

CALCULATION EXAMPLE 5 (Fractionated Plasma)

A PMB concentration in the plasma of 0.15 µg/ml is to be obtained by the use of the PMB-coated adsorber CG161c in the extracorporeal blood circuit. Due to preliminary tests (See FIG. 24), the function describing the correlation between coated PMB quantity per g adsorber and desorbed PMB quantity in the fractionated plasma was able to be determined by way of experiment. In this case, this is as follows:

$$PMB\left[\frac{mg}{g\ adsorber}\right] = 2.6718\ln(x) - 3.3628$$

x=desired PMB concentration in plasma=0.15 µg/ml=150 ng/ml

If x=150 ng/ml used, the PMB quantity that must be bonded hydrophobically per g adsorber is: 10.025 mg pro g adsorber (CG161c)

CALCULATION EXAMPLE 6 (Fractionated Plasma)

A PMB concentration in the plasma of 0.8 µg/ml is to be obtained by the use of the PMB-coated adsorber CG161c in the extracorporeal blood circuit. Due to preliminary tests (See FIG. 24), the function describing the correlation between coated PMB quantity per g adsorber and desorbed PMB quantity in the fractionated plasma was able to be determined by way of experiment. In this case, this is as follows:

$$PMB\left[\frac{mg}{g\ adsorber}\right] = 2.6718\ln(x) - 3.3628$$

x=desired PMB concentration in plasma=0.8 µg/ml=800 ng/ml

If x=800 ng/ml used, the PMB quantity that must be bonded hydrophobically per g adsorber is: 14.497 mg pro g adsorber (CG161c)

10. EXAMPLE 10: Polymyxin B (PMB) Desorption Over Time

This test is intended to demonstrate that the equilibrium reaction (adsorption and desorption of polymyxin (B)) is quick and stable in plasma.

10.1 Carrier

HPR10: the carrier HPR10 (Rohm & Haas/Dow Chemical Company; also referred to hereinafter as adsorber) consists of a porous polystyrene-divinylbenzene matrix. The average pore size is 30-40 nm, the average particle size is 10 j m and the accessible surface is 500 $m^2$/g carrier (dry). The dry weight per ml moist carrier is 30% (w/v).

10.2 Coating of the Carrier with Polymyxin B (PMB)

The PMB solution (Sigma, 10 mg/ml in dist. water) is autoclaved at 121° C. for 30 min, and the carrier (HPR10) is then coated in 15 ml Greiner tubes with PMB as follows (see Table 10.2): 3 ml carrier with 7.5 ml PMB solution

TABLE 10.2

The carrier/adsorber is coated with different quantities of PMB

| PMB coating in mg per ml adsorber | Adsorber [ml] | PMB solution [ml] | NaCl [ml] |
|---|---|---|---|
| 5 | 3 | 1.5 | 6 |
| 10 | 3 | 3 | 4.5 |
| 25 | 3 | 0 | 7.5 |

The coating is carried out overnight on a roll mixer at room temperature. The coated carrier is then washed twice with 10 ml NaCl solution (sterile), and a 50% suspension is produced. A tube without adsorber was included as control.

10.3 Batch Test

The plasma with 5 IU heparin is spiked with 5 ng/ml LPS (L-7018 *Pseud. aerug.* company Sigma batch: 128K4115). In the triplicate approach, 1% PMB-coated carrier is incubated with the LPS-spiked plasma (30 µl carrier+2970 µl LPS spiked plasma) at 37° C. in an overhead shaker and samples were taken at intervals (5, 15 and 60 min) for LAL analysis.

10.4 Analysis

The analysis was performed using an LAL test.

Used Materials for Batch Test and LAL Tests:

| | | Batch: |
|---|---|---|
| Microtiter plates MT 1007 | company Charles River | 1721599k.A. |
| Lal test tubes T 200 | Ch. River Endosafe | 53351 Dk.A. |
| Combitips plus 5 ml Biopur | Eppendorf | X131667I |
| Pipette tips | Eppendorf | V125542M |
| Pipette tips | Eppendorf | W130324Q |
| NaCl 0.9% | Mayerhofer | 8G5523 2011-07 |
| Microcentrifuge tubes | Greiner | 05200108 |
| Charles RiverEndosafe | Endochrome | Kit. batch: A2112EK1 |

10.5 Result

Figure 25:
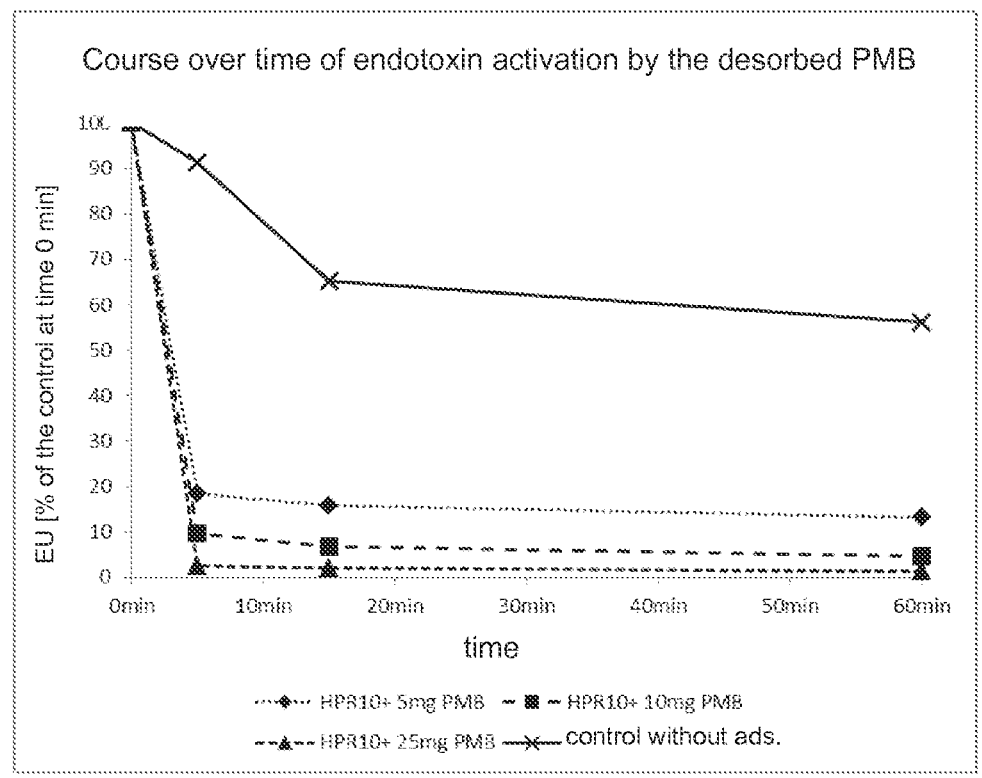
FIG. 25 shows the equilibrium concentration of desorbed PMB in the plasma over time.

The equilibrium concentration of desorbed PMB in the plasma is attained very quickly. The LPS inactivation after 5 minutes is almost the same as after 60 minutes of incubation (see FIG. 25).

11. EXAMPLE 11: Influence of the Coating of a Carrier Coated with Polymyxin B (PMB) on Cytokine Adsorption 11.1 Test Description The extent to which the PMB-coated adsorber CG161c is suitable for the adsorption of cytokines compared with the uncoated adsorber CG161c was tested in a 10% (v/v) batch test. 5 ng/ml endotoxin (LPS) from *Pseudomonas aeruginosa* were also added.

11.2 Test Structure

Carrier:

Amberchrom CG161 (mean particle size 120 am, mean pore size 15 nm)

Coating with PMB:

The PMB solution (Sigma Aldrich, 10 mg/ml in dist. water) and the carrier in 50% suspension are coated in 15 ml Greiner tubes with PMB as follows (Table 11.2.1):

TABLE 11.2.1

| | 50% adsorber suspension [ml] | PMB solution [ml] | NaCl [ml] |
|---|---|---|---|
| 3xapproach | 2 | 1 | 2 |

The coating was performed overnight on an Enviro-Genie (25:50) at room temperature. The carrier was then washed twice with 10 ml NaCl solution (sterile), and a 50% suspension was produced.

Batch Approach:

Triplicate approach: in each case 1 ml adsorber (moist)+9 ml spike 15 ml Greiner tubes are shaken in the Enviro-Genie for 60 min at 25/50 rpm at 37° C.

Cytokines:

The stock solution is diluted 1:10 in plasma (freshly frozen plasma, plasma donor centre Retz) (1:10; 5 µL stock+45 µL plasma). The end concentration of the plasma spike (100 mL) for the used cytokines is presented in Table 11.2.2 below:

TABLE 11.2.2

| Batch Nr | Stock concentration [µg/mL] | Stock dilution 1:10 | Stock dilution to plasma [100 mL] | End concentration in the plasma [pg/mL] |
|---|---|---|---|---|
| TNF-α | 10 | 5 µL + 45 µl | 15 µL | 500 |
| IL-1α | 5 | 5 µL + 45 µl | 65 µL | 250 |
| IL-6 | 10 | 5 µL + 45 µl | 35 µL | 200 |
| IL-8 | 10 | 5 µL + 45 µl | 35 µL | 200 |
| IL-10 | 10 | 5 µL + 45 µl | 40 µL | 300 |

Endotoxins (LPS):

*Pseudomonas aeruginosa*: L-7018 company Sigma batch: 128K4115, −70° C., at 100 µl 10−3 g/ml (1 mg/ml).

LPS is used in the batch with a final concentration of 5 ng/ml

→50 µl $10^{-5}$ solution in 100 ml plasma (Tables 11.2.3 and 11.2.4)

TABLE 11.2.3

| $10^{-4}$ | $10^{-5}$ | |
|---|---|---|
| 0.9 | 0.900 | NaCl |
| 0.1 | 0.100 | LPS |
| 100 µg/ml | 10 µg/ml | LPS concentration |

TABLE 11.2.4

| | 0 min | 60 min |
|---|---|---|
| Spike without adsorber | 1 | 2 |
| CG161c - 1 without PMB | | 3 |
| CG161c - 2 without PMB | | 4 |
| CG161c - 3 without PMB | | 5 |
| CG161c - 4 with PMB | | 6 |
| CG161c - 5 with PMB | | 7 |
| CG161c - 6 with PMB | | 8 |

=8 samples, that is to say 100 ml citrate plasma spikes 11.3 Analysis

The cytokine analysis is performed with the aid of a Luminex apparatus (based on antibodies) from the company Biorad.

11.4 Results

Figure 26:
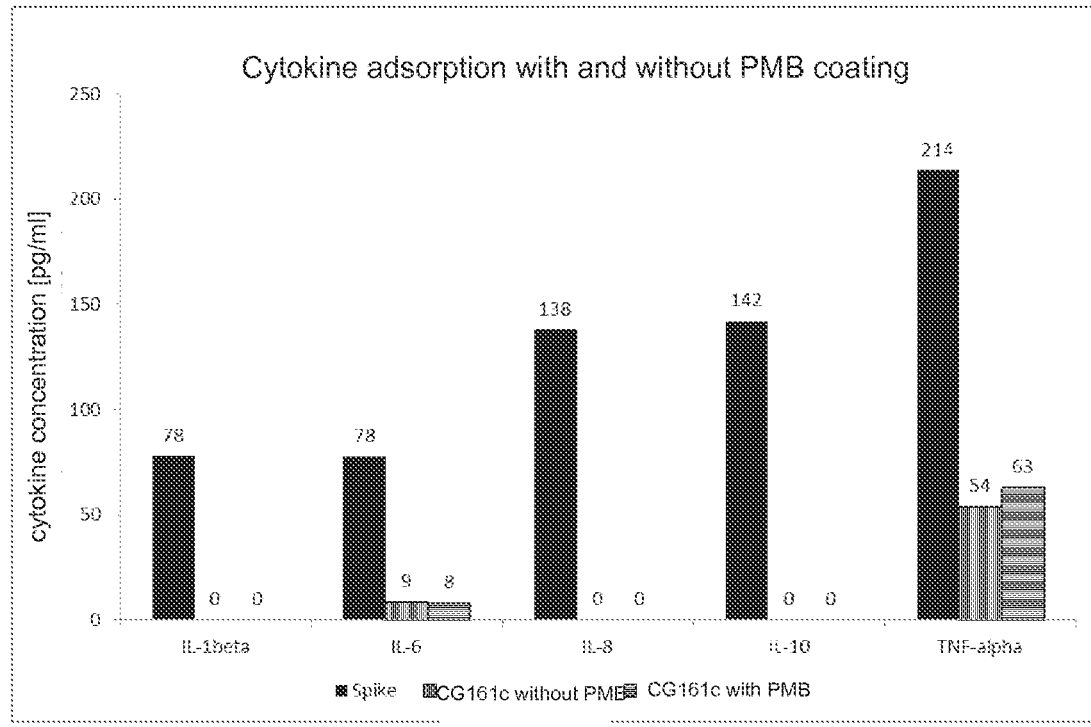
FIG. 26 shows cytokine analysis performed with the aid of a Luminex apparatus.

The results are shown in FIG. 26, from which it can be clearly seen that an adsorptive coating of the carrier surface with polymyxin B has no effects on the adsorption of the cytokines.

The invention claimed is:

1. An extracorporeal perfusion apparatus comprising an extracorporeal blood circuit for conveying blood, a filtrate circuit for conveying blood plasma, and a controller,
  wherein the filtrate circuit is connected to the extracorporeal blood circuit via a filter, wherein the filter has a sieving coefficient of 5% for substances having a molar mass of 340,000 g/mol (relative molecular mass of 340 kDa), and
  wherein a depletion agent comprising a first carrier having a neutral, hydrophobic surface is arranged in the filtrate circuit, and
  wherein the extracorporeal perfusion apparatus comprises a dispenser provided separately from the filter for feeding an endotoxin-binding lipopeptide into the extracorporeal blood circuit, wherein the endotoxin-binding lipopeptide is selected from the group consisting of polymyxins, polymyxin derivatives, prodrugs thereof, and a combination thereof.

2. The extracorporeal perfusion apparatus according to claim 1, wherein the endotoxin-binding lipopeptide is a polymyxin selected from the group consisting of polymyxin B, Colistin, and prodrugs thereof.

3. The extracorporeal perfusion apparatus according to claim 1, wherein the depletion agent comprises the dispenser configured to feed the endotoxin-binding lipopeptide, wherein the surface of the first carrier has an adsorptive coating formed of the endotoxin-binding lipopeptide.

4. The extracorporeal perfusion apparatus according to claim 3, wherein the endotoxin-binding lipopeptide adsorbed at the surface of the first carrier is present in a quantity that, when the lipopeptide is fed, gives a lipopeptide serum concentration from 0.01 µg/ml to 0.8 µg/ml.

5. The extracorporeal perfusion apparatus according to claim 3, wherein the first carrier has a total surface from 100 to 1500 m²/g, wherein 50 to 2000 mg of endotoxin-binding lipopeptide in relation to the total carrier surface are bonded adsorptively at the surface of the first or second carrier.

6. The extracorporeal perfusion apparatus according to claim 3, wherein the filtrate circuit leads into the filter, and in that the first carrier has the form of microparticles and the filtrate circuit comprises a suspension of these microparticles, wherein the microparticles have a mean particle size of 20 µm or smaller.

7. The extracorporeal perfusion apparatus according to claim 1, wherein the dispenser configured to feed the endotoxin-binding lipopeptide is arranged in the filtrate circuit downstream of the depletion agent, wherein the dispenser comprises a second carrier having a neutral, hydrophobic surface, wherein the surface of the second carrier has an adsorptive coating formed of the endotoxin-binding lipopeptide.

8. The extracorporeal perfusion apparatus according to claim 1, wherein the dispenser configured to feed the endotoxin-binding lipopeptide comprises a dosing device for feeding the endotoxin-binding lipopeptide into the extracorporeal blood circuit at a lipopeptide feed point associated with the extracorporeal blood circuit.

9. The extracorporeal perfusion apparatus according to claim 8, wherein the lipopeptide feed point is arranged in the extracorporeal blood circuit downstream of the filter.

10. The extracorporeal perfusion apparatus according to claim 9, wherein a dialyser is arranged in the extracorporeal blood circuit downstream of the filter, wherein the lipopeptide feed point is arranged in the extracorporeal blood circuit downstream of the dialyser.

11. The extracorporeal perfusion apparatus according to claim 9, wherein a sensor configured to measure the concentration of the endotoxin-binding lipopeptide is arranged downstream of the filter or of the dialyser and upstream of the lipopeptide feed point.

12. The extracorporeal perfusion apparatus according to claim 8, wherein the controller of the perfusion apparatus is configured, when the lipopeptide is dosed into the blood conveyed in the extracorporeal blood circuit, to take into consideration the lipopeptide clearance of the body, the lipopeptide clearance of the depletion agent and/or the lipopeptide clearance of the dialyser.

13. The extracorporeal perfusion apparatus according to claim 1, wherein the dispenser configured to feed the endotoxin-binding lipopeptide comprises a dialyser arranged in the extracorporeal blood circuit downstream of the filter, said dialyser being configured to supply the endotoxin-binding lipopeptide to the extracorporeal blood circuit using a dialysis fluid conveyed through the dialyser.

14. The extracorporeal perfusion apparatus according to claim 1, wherein the first carrier is formed from a neutral polymer.

15. The extracorporeal perfusion apparatus according to claim 14, wherein the polymer is selected from a cross-linked polystyrene polymer or a cross-linked ethylene divinylbenzene polymer.

16. The extracorporeal perfusion apparatus according to claim 1, wherein the first carrier is porous and has a mean pore size of 100 nm or less.

17. The extracorporeal perfusion apparatus according to claim 16, wherein the first carrier has a mean pore size of 20 nm or less or a mean pore size from 80 to 100 nm.

18. The extracorporeal perfusion apparatus according to claim 1, wherein the first carrier is fibre-like or is in particle form.

19. The extracorporeal perfusion apparatus according to claim 18, wherein the first carrier has the form of microparticles having a mean particle size of 300 μm or smaller.

20. The extracorporeal perfusion apparatus according to claim 19, wherein the first carrier has a mean pore size from one of either 10 nm to 20 nm or 80 nm to 100 nm and a mean particle size from 75 to 150 μm.

* * * * *